US009652655B2

(12) United States Patent
Satish et al.

(10) Patent No.: US 9,652,655 B2
(45) Date of Patent: *May 16, 2017

(54) SYSTEM AND METHOD FOR ESTIMATING EXTRACORPOREAL BLOOD VOLUME IN A PHYSICAL SAMPLE

(75) Inventors: Siddarth Satish, Cupertino, CA (US); Kevin Miller, Lawrenceville, NJ (US); Ali Zandifar, San Francisco, CA (US)

(73) Assignee: Gauss Surgical, Inc., Los Altos, CA (US)

( * ) Notice: Subject to any disclaimer, the term of this patent is extended or adjusted under 35 U.S.C. 154(b) by 1194 days.

This patent is subject to a terminal disclaimer.

(21) Appl. No.: 13/544,664

(22) Filed: Jul. 9, 2012

(65) Prior Publication Data
US 2013/0010094 A1 Jan. 10, 2013

Related U.S. Application Data

(60) Provisional application No. 61/506,082, filed on Jul. 9, 2011, provisional application No. 61/646,818, filed
(Continued)

(51) Int. Cl.
*G06K 9/00* (2006.01)
*G06T 7/60* (2017.01)
(Continued)

(52) U.S. Cl.
CPC ............... *G06K 9/00* (2013.01); *G06T 5/00* (2013.01); *G06T 7/602* (2013.01);
(Continued)

(58) Field of Classification Search
CPC ...... A61B 5/15; A61B 5/150007; A61B 5/157; A61B 5/02042; A61B 5/150992;
(Continued)

(56) References Cited

U.S. PATENT DOCUMENTS 2,707,955 A 5/1955 Borden
3,182,252 A 5/1965 Den Berg
(Continued)

FOREIGN PATENT DOCUMENTS

CA 2870635 A1 10/2013
CN 101505813 8/2009
(Continued)

OTHER PUBLICATIONS

Sant, et al. "Exsanguinated Blood Volume Estimation Using Fractal Analysis of Digital Images." Journal of Forensic Sciences 57.3 (2012): 610-17. Print.*
(Continued)

*Primary Examiner* — Michael A. Newman

(57) ABSTRACT

One method for estimating the extracorporeal blood volume in a portion of a physical sample includes: extracting a feature from a portion of an image of the sample; tagging the portion of the image of the sample with a blood volume indicator according to the extracted feature; and estimating the extracorporeal blood volume in at least the portion of the physical sample, associated with the portion of the image of the sample, according to the blood volume indicator.

42 Claims, 13 Drawing Sheets

Related U.S. Application Data on May 14, 2012, provisional application No. 61/646,814, filed on May 14, 2012.

(51) Int. Cl.
 *G06T 5/00* (2006.01)
 *A61B 5/02* (2006.01)

(52) U.S. Cl.
 CPC . *A61B 5/02042* (2013.01); *G06T 2207/10024* (2013.01); *G06T 2207/30004* (2013.01)

(58) Field of Classification Search
 CPC .......... G06T 7/062; G06T 2207/30004; G06K 9/00885; G06K 9/685
 USPC ......... 382/128, 134, 171, 209, 190; 604/404
 See application file for complete search history.

(56) References Cited

U.S. PATENT DOCUMENTS

| | | | |
|---|---|---|---|
| 3,199,507 A | 8/1965 | Kamm | |
| 3,367,431 A | 2/1968 | Prindle Baker | |
| 3,646,938 A | 3/1972 | Haswell | |
| 3,832,135 A | 8/1974 | Chlupsa et al. | |
| 3,864,571 A | 2/1975 | Stillman et al. | |
| 3,948,390 A | 4/1976 | Ferreri | |
| 4,105,019 A | 8/1978 | Haswell | |
| 4,149,537 A | 4/1979 | Haswell | |
| 4,244,369 A | 1/1981 | McAvinn et al. | |
| 4,402,373 A | 9/1983 | Comeau | |
| 4,422,548 A | 12/1983 | Cheesman et al. | |
| 4,429,789 A | 2/1984 | Puckett | |
| 4,562,842 A | 1/1986 | Morfeld et al. | |
| 4,583,546 A | 4/1986 | Garde | |
| 4,773,423 A | 9/1988 | Hakky | |
| 4,784,267 A | 11/1988 | Gessler et al. | |
| 4,832,198 A | 5/1989 | Alikhan | |
| 4,917,694 A | 4/1990 | Jessup | |
| 4,922,922 A | 5/1990 | Pollock et al. | |
| 5,029,584 A | 7/1991 | Smith | |
| 5,031,642 A * | 7/1991 | Nosek | 600/584 |
| 5,048,683 A | 9/1991 | Westlake | |
| 5,119,814 A | 6/1992 | Minnich | |
| 5,190,059 A | 3/1993 | Fabian et al. | |
| 5,231,032 A | 7/1993 | Ludvigsen | |
| 5,236,664 A | 8/1993 | Ludvigsen | |
| 5,285,682 A | 2/1994 | Micklish | |
| 5,492,537 A | 2/1996 | Vancaillie | |
| 5,522,805 A | 6/1996 | Vancaillie et al. | |
| 5,629,498 A * | 5/1997 | Pollock et al. | 177/15 |
| 5,633,166 A | 5/1997 | Westgard et al. | |
| 5,650,596 A | 7/1997 | Morris et al. | |
| 5,709,670 A | 1/1998 | Vancaillie et al. | |
| 5,807,358 A | 9/1998 | Herweck et al. | |
| 5,851,835 A | 12/1998 | Groner | |
| 5,923,001 A | 7/1999 | Morris et al. | |
| 5,931,824 A | 8/1999 | Stewart et al. | |
| 5,944,668 A | 8/1999 | Vancaillie et al. | |
| 5,956,130 A | 9/1999 | Vancaillie et al. | |
| 5,984,893 A | 11/1999 | Ward | |
| 5,996,889 A | 12/1999 | Fuchs et al. | |
| 6,006,119 A | 12/1999 | Soller et al. | |
| 6,061,583 A | 5/2000 | Ishihara et al. | |
| 6,359,683 B1 | 3/2002 | Berndt | |
| 6,510,330 B1 | 1/2003 | Enejder | |
| 6,641,039 B2 | 11/2003 | Southard | |
| 6,728,561 B2 | 4/2004 | Smith et al. | |
| 6,730,054 B2 | 5/2004 | Pierce et al. | |
| 6,777,623 B2 | 8/2004 | Ballard | |
| 6,998,541 B2 | 2/2006 | Morris et al. | |
| 7,001,366 B2 | 2/2006 | Ballard | |
| 7,112,273 B2 | 9/2006 | Weigel et al. | |
| 7,147,626 B2 | 12/2006 | Goodman et al. | |
| 7,158,030 B2 | 1/2007 | Chung | |
| 7,180,014 B2 | 2/2007 | Farber et al. | |
| 7,274,947 B2 | 9/2007 | Koo et al. | |
| 7,297,834 B1 | 11/2007 | Shapiro | |
| 7,299,981 B2 | 11/2007 | Hickle et al. | |
| 7,364,545 B2 | 4/2008 | Klein | |
| 7,384,399 B2 | 6/2008 | Ghajar | |
| 7,430,047 B2 | 9/2008 | Budd et al. | |
| 7,430,478 B2 | 9/2008 | Fletcher-Haynes et al. | |
| 7,469,727 B2 | 12/2008 | Marshall | |
| 7,499,581 B2 | 3/2009 | Tribble et al. | |
| 7,557,710 B2 | 7/2009 | Sanchez et al. | |
| 7,641,612 B1 | 1/2010 | McCall | |
| D611,731 S | 3/2010 | Levine | |
| 7,670,289 B1 | 3/2010 | McCall | |
| 7,703,674 B2 | 4/2010 | Stewart et al. | |
| 7,708,700 B2 | 5/2010 | Ghajar | |
| 7,711,403 B2 | 5/2010 | Jay et al. | |
| 7,749,217 B2 * | 7/2010 | Podhajsky | 606/34 |
| 7,795,491 B2 | 9/2010 | Stewart et al. | |
| 7,819,818 B2 | 10/2010 | Ghajar | |
| 7,909,806 B2 | 3/2011 | Goodman et al. | |
| 7,966,269 B2 | 6/2011 | Bauer et al. | |
| 7,995,816 B2 * | 8/2011 | Roger et al. | 382/128 |
| 8,025,173 B2 | 9/2011 | Michaels | |
| 8,105,296 B2 | 1/2012 | Morris et al. | |
| 8,181,860 B2 * | 5/2012 | Fleck et al. | 235/380 |
| 8,194,235 B2 | 6/2012 | Kosaka et al. | |
| 8,279,068 B2 | 10/2012 | Morris et al. | |
| 8,398,546 B2 | 3/2013 | Pacione et al. | |
| 8,472,693 B2 | 6/2013 | Davis et al. | |
| 8,479,989 B2 | 7/2013 | Fleck et al. | |
| 8,576,076 B2 | 11/2013 | Morris et al. | |
| 8,626,268 B2 | 1/2014 | Adler et al. | |
| 8,693,753 B2 | 4/2014 | Nakamura | |
| 8,704,178 B1 | 4/2014 | Pollock et al. | |
| 8,792,693 B2 * | 7/2014 | Satish | G06K 9/00 356/39 |
| 8,897,523 B2 | 11/2014 | Satish et al. | |
| 8,983,167 B2 | 3/2015 | Satish et al. | |
| 9,171,368 B2 | 10/2015 | Satish et al. | |
| 2003/0095197 A1 | 5/2003 | Wheeler et al. | |
| 2003/0130596 A1 | 7/2003 | Goltz | |
| 2004/0031626 A1 | 2/2004 | Morris et al. | |
| 2004/0129678 A1 | 7/2004 | Crowley et al. | |
| 2005/0051466 A1 | 3/2005 | Carter et al. | |
| 2005/0163354 A1 | 7/2005 | Ziegler | |
| 2006/0058593 A1 | 3/2006 | Drinan et al. | |
| 2006/0178578 A1 | 8/2006 | Tribble et al. | |
| 2006/0224086 A1 | 10/2006 | Harty | |
| 2007/0004959 A1 | 1/2007 | Carrier et al. | |
| 2007/0287182 A1 | 12/2007 | Morris et al. | |
| 2008/0029416 A1 | 2/2008 | Paxton | |
| 2008/0030303 A1 | 2/2008 | Kobren et al. | |
| 2008/0045845 A1 | 2/2008 | Pfeiffer et al. | |
| 2008/0194906 A1 | 8/2008 | Mahony et al. | |
| 2009/0076470 A1 | 3/2009 | Ryan | |
| 2009/0310123 A1 | 12/2009 | Thomson | |
| 2009/0317002 A1 | 12/2009 | Dein | |
| 2010/0003714 A1 | 1/2010 | Bachur, Jr. et al. | |
| 2010/0007727 A1 | 1/2010 | Torre-Bueno | |
| 2010/0025336 A1 | 2/2010 | Carter et al. | |
| 2010/0027868 A1 | 2/2010 | Kosaka et al. | |
| 2010/0066996 A1 | 3/2010 | Kosaka et al. | |
| 2010/0087770 A1 * | 4/2010 | Bock | A61M 1/3656 604/4.01 |
| 2010/0280117 A1 | 11/2010 | Patrick et al. | |
| 2011/0192745 A1 | 8/2011 | Min | |
| 2011/0196321 A1 | 8/2011 | Wudyka | |
| 2011/0200239 A1 | 8/2011 | Levine et al. | |
| 2011/0275957 A1 | 11/2011 | Bhandari | |
| 2011/0305376 A1 | 12/2011 | Neff | |
| 2011/0316973 A1 | 12/2011 | Miller et al. | |
| 2012/0000297 A1 * | 1/2012 | Hashizume et al. | 73/863.02 |
| 2012/0065482 A1 | 3/2012 | Robinson et al. | |
| 2012/0210778 A1 | 8/2012 | Palmer et al. | |
| 2012/0257188 A1 | 10/2012 | Yan et al. | |
| 2012/0262704 A1 | 10/2012 | Zahniser et al. | |
| 2012/0309636 A1 | 12/2012 | Gibbons et al. | |
| 2013/0010094 A1 | 1/2013 | Satish et al. | |
| 2013/0170729 A1 | 7/2013 | Wardlaw et al. | |

(56) References Cited

U.S. PATENT DOCUMENTS

| | | |
|---|---|---|
| 2013/0301901 A1 | 11/2013 | Satish et al. |
| 2013/0303870 A1 | 11/2013 | Satish et al. |
| 2013/0308852 A1 | 11/2013 | Hamsici et al. |
| 2014/0079297 A1 | 3/2014 | Tadayon et al. |
| 2014/0330094 A1 | 11/2014 | Pacione et al. |
| 2015/0294460 A1 | 10/2015 | Satish et al. |
| 2016/0027173 A1 | 1/2016 | Satish et al. |

FOREIGN PATENT DOCUMENTS

| | | |
|---|---|---|
| JP | S-59/161801 U | 10/1984 |
| JP | S-62-144652 U | 6/1987 |
| JP | H06510210 A | 11/1994 |
| JP | H11-37845 A | 2/1999 |
| JP | 2002-331031 A | 11/2002 |
| JP | 2003-075436 A | 3/2003 |
| JP | 3701031 B2 | 9/2005 |
| JP | 2005-052288 A | 10/2006 |
| JP | 2006-280445 A | 3/2008 |
| JP | 2008-055142 A | 3/2008 |
| JP | 2011-515681 A | 5/2011 |
| WO | 9217787 A1 | 10/1992 |
| WO | 9639927 A1 | 12/1996 |
| WO | WO 2009/117652 A1 | 9/2009 |
| WO | 2011019576 A1 | 2/2011 |
| WO | 2013009709 A | 1/2013 |
| WO | 2013172874 A | 11/2013 |
| WO | 2013173356 A | 11/2013 |

OTHER PUBLICATIONS

Bellad, et al. "Standardized Visual Estimation of Blood Loss during Vaginal Delivery with Its Correlation Hematocrit Changes—A Descriptive Study." South Asian Federation of Obstetrics and Gynecology 1.1 (2009): 29-34. Web.*
Aklilu, A. Gauss Surgical Measures Blood Loss with a Smartphone. Jun. 14, 2012. <http://www.health2con.com/news/2012/06/14/gauss-surgical-measures-blood-loss-with-a-smartphone/>.
Kamiyoshihara, M. et al. The Utility of an Autologous Blood Salvage System in Emergency Thoracotomy for a emothorax After Chest Trauma. Gen. Thorac. Cargiovasc. Surg. (2008); vol. 56, p. 222.
Pogorelc, D. iPads in the OR: New Mobile Platform to Monitor Blood Loss During Surgery. Jun. 6, 2012. <http://medcitynews.com/2012/06/ipads-in-the-or-new-mobile-platform-to-monitor-blood-loss-during-surgery/>.
ACOG (2012). "Optimizing protocols in obstetrics," Series 2, 25 total pages.
Adkins, A.R. et al. (2014). "Accuracy of blood loss estimations among anesthesia providers," *AANA Journal* 82(4):300-306.
Al-Kadri, H.M. et al. (2014). "Effect of education and clinical assessment on the accuracy of post partum blood loss estimation," *BMC Preg. Childbirth* 14:110, 7 total pages.
Awhonn Practice Brief (2014). "Quantification of blood loss: AWHONN practice brief No. 1," *AWHONN* p. 1-3.
Bose, P. et al. (2006). "Improving the accuracy of estimated blood loss at obstetric haemorrhage using clinical reconstructions," *BJOG* 113(8):919-924.
Eipe, N. et al. (2006). "Perioperative blood loss assessment—How accurate?" *Indian J. Anaesth.* 50(1):35-38.
Extended European Search Report mailed on Apr. 1, 2015, for EP Application No. 12 810 640.8, filed on Jul. 9, 2012, 8 pages.
Extended European Search Report mailed on Nov. 23, 2015, for EP Application No. 13 790 688.9, filed on May 14, 2013, 9 pages.
Extended European Search Report mailed on Nov. 17, 2015, for EP Application No. 13 790 449.6, filed on Jan. 10, 2013, 8 pages.
Final Office Action mailed on Aug. 26, 2016, for U.S. Appl. No. 13/894,054, filed on May 14, 2013, 7 pages.
Final Office Action mailed on Jul. 26, 2016, for U.S. Appl. No. 14/876,628, filed on Oct. 6, 2015, 5 pages.

Habak, P.J. et al. (2016). "A comparison of visual estimate versus calculated estimate of blood loss at vaginal delivery," *British J. Med. Medical Res.* 11(4):1-7.
Holmes, A.A. (2014). "Clinical evaluation of a novel system for monitoring surgical hemoglobin loss," *Anesth. Analg.* 119(3):588-594.
International Search Report mailed on Sep. 17, 2012, for PCT Application No. PCT/US2012/045969, filed on Jul. 9, 2012, 2 pages.
International Search Report mailed on Sep. 24, 2013, for PCT Application No. PCT/US2013/040976, filed on May 14, 2013, 2 pages.
International Search Report mailed on Mar. 26, 2013, for PCT Application No. PCT/US2013/021075, filed on Jan. 10, 2013, 2 pages.
International Search Report mailed on Jul. 24, 2015, for PCT Application No. PCT/US2015/026036, filed on Apr. 15, 2015, 2 pages.
Jones, R. (2015). "Quantitative measurement of blood loss during delivery," *AWHONN* p. S41.
Lyndon, A. et al. (2010). "Blood loss: Clinical techniques for ongoing quantitative measurement," *CMQCC Obstetric Hemorrhage Toolkit*, pp. 1-7.
Lyndon, A. et al. (2015). "Cumulative quantitative assessment of blood loss," *CMQCC Obstetric Hemorrhage Toolkit Version 2.0*, pp. 80-85.
Manikandan, D. et al. (2015). "Measurement of blood loss during adenotonsillectomy in children and factors affecting it," *Case Reports in Clinical Medicine* 4:151-156.
Merck for Mother's Program (2012). Blood loss measurement: Technology opportunity assessment, 9 total pages.
Non-Final Office Action mailed on May 9, 2014, for U.S. Appl. No. 13/544,679, filed on Jul. 9, 2012, 7 pages.
Non-Final Office Action mailed on Mar. 30, 2016, for U.S. Appl. No. 13/894,054, filed on May 14, 2013, 9 pages.
Non-Final Office Action mailed on Sep. 5, 2014, for U.S. Appl. No. 13/738,919, filed on Jan. 10, 2013, 8 pages.
Non-Final Office Action mailed on Mar. 20, 2015, for U.S. Appl. No. 14/613,807, filed on Feb. 4, 2015, 8 pages.
Non-Final Office Action mailed on Dec. 15, 2015, for U.S. Appl. No. 14/876,628, filed on Oct. 6, 2015, 8 pages.
Notice of Allowance mailed on May 12, 2014, for U.S. Appl. No. 13/544,646, filed on Jul. 9, 2012, 10 pages.
Notice of Allowance mailed on Sep. 3, 2014, for U.S. Appl. No. 13/544,679, filed on Jul. 9, 2012, 8 pages.
Notice of Allowance mailed on Nov. 10, 2014, for U.S. Appl. No. 13/738,919, filed on Jan. 10, 2013, 10 pages.
Notice of Allowance mailed on Jun. 25, 2015, for U.S. Appl. No. 14/613,807, filed on Feb. 4, 2015, 10 pages.
Notice of Allowance mailed on Oct. 26, 2016, for U.S. Appl. No. 14/876,628, filed on Oct. 6, 2015, 11 pages.
Roston, A.B. et al. (2012). Chapter 9: Blood loss: Accuracy of visual estimation, pp. 71-72.
Schorn, M.N. (2010). "Measurement of blood loss: Review of the literature," *J. Midwifery and Women's Health* 55(1):20-27.
Sukprasert, M. et al. (2006). "Increase accuracy of visual estimation of blood loss from education programme," *J. Med. Assoc. Thai* 89(suppl. 4):554-559.
Written Opinion of the International Searching Authority mailed on Sep. 17, 2012, for PCT Application No. PCT/US2012/045969, filed on Jul. 9, 2012, 4 pages.
Written Opinion of the International Searching Authority mailed on Sep. 24, 2013, for PCT Application No. PCT/US2013/040976, filed on May 14, 2013, 4 pages.
Written Opinion of the International Searching Authority mailed on Mar. 26, 2013, for PCT Application No. PCT/US2013/021075, filed on Jan. 10, 2013, 6 pages.
Written Opinion of the International Searching Authority mailed on Jul. 24, 2015, for PCT Application No. PCT/US2015/026036, filed on Apr. 15, 2015, 6 pages.

\* cited by examiner

SYSTEM AND METHOD FOR ESTIMATING EXTRACORPOREAL BLOOD VOLUME IN A PHYSICAL SAMPLE

CROSS-REFERENCE TO RELATED APPLICATIONS

This application claims the benefit of U.S. Provisional Patent Application Ser. No. 61/506,082, filed 9 Jul. 2011, U.S. Provisional Patent Application Ser. No. 61/646,818, filed 14 May 2012, and U.S. Provisional Patent Application Ser. No. 61/646,814, filed 14 May 2012, all of which are herein incorporated in their entireties by this reference.

TECHNICAL FIELD

This invention relates generally to the surgical field, and more specifically to a new and useful system and method for estimating the extracorporeal blood volume in a physical sample for use in surgical practice.

BACKGROUND

Overestimation and underestimation of patient blood loss is a significant contributor to high operating and surgical costs for hospitals, clinics and other medical facilities. Specifically, overestimation of patient blood loss results in wasted transfusion-grade blood and higher operating costs for medical institutions and can lead to blood shortages. Underestimation of patient blood loss is a key contributor of delayed resuscitation and transfusion in the event of hemorrhage and has been associated with billions of dollars in avoidable patient infections, re-hospitalizations, and lawsuits annually. Thus, there is a need in the surgical field for a new and useful system and method for estimating extracorporeal blood volume in a physical sample. This invention provides such a new and useful system and method.

DESCRIPTION OF THE PREFERRED EMBODIMENTS

The following description of preferred embodiments of the invention is not intended to limit the invention to these preferred embodiments, but rather to enable any person skilled in the art to make and use this invention.

1. First Method

Figure 1A:
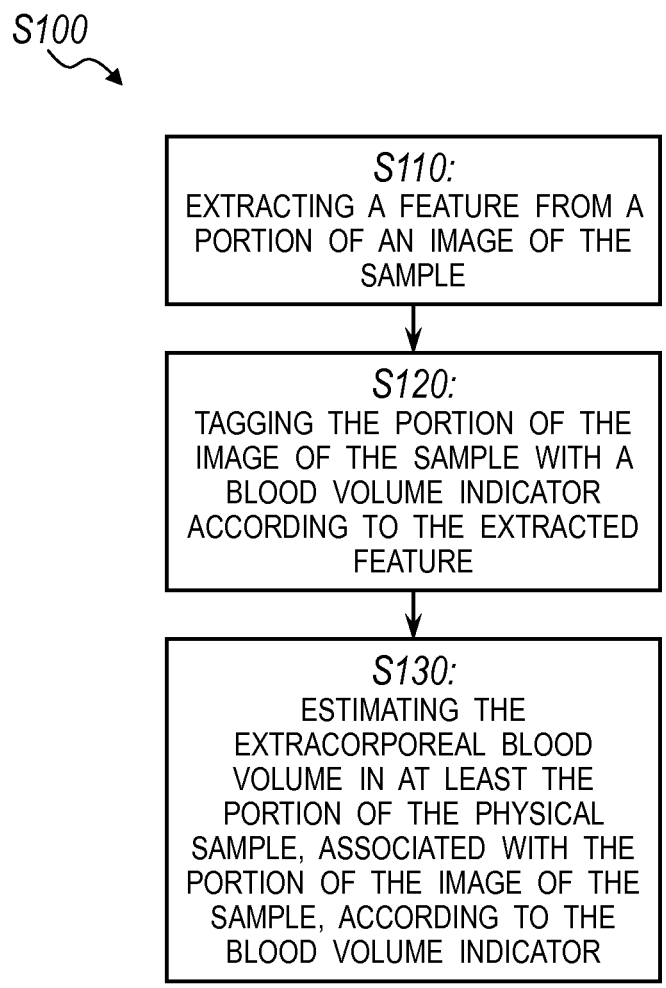
FIG. 1A is a flowchart representation of a method of a first preferred embodiment.

As shown in FIG. 1A, a method S100 of a preferred embodiment for estimating the extracorporeal blood volume in a portion of a physical sample includes: extracting a feature from a portion of an image of the sample in Block S110; tagging the portion of the image of the sample with a blood volume indicator according to the extracted feature in Block S120; and estimating the extracorporeal blood volume in at least the portion of the physical sample, associated with the portion of the image of the sample, according to the blood volume indicator in Block S130.

Figure 7:
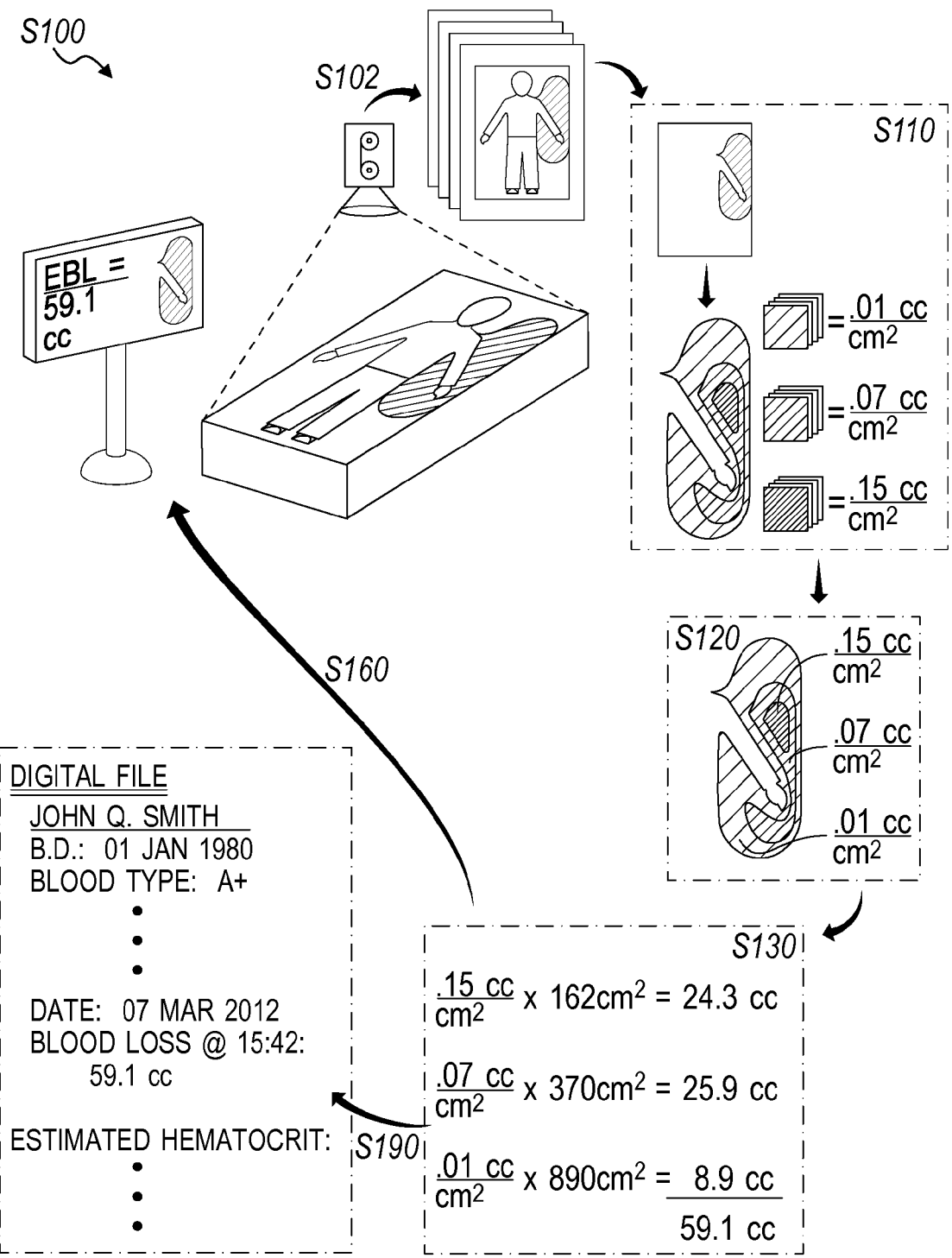
FIG. 7 is a flowchart representation of another variation of the preferred method.

As shown in FIG. 7, the first preferred method S100 preferably functions to estimate the volume of blood in the physical sample by analyzing an image of the sample. The image of the sample is preferably a color frame of a live video feed, wherein at least a portion of the physical sample is visible in the frame. However, the image can alternatively be a static or still image, an infrared image, a field of view of an optical sensor, a black and white image, a fingerprint of a field of view of an optical sensor, a point cloud, or any other suitable type of image. In situations in which the physical sample does not fit within a field of view of the camera or optical sensor, the image can be a scan of the physical sample. The image can be captured and then stored on a local or remote data storage device for subsequent processing, though the image can alternatively or in parallel be processed in real time, or in parts or segments to avoid storage of the full image. The first preferred method S100 preferably estimates an extracorporeal blood volume that includes blood external the body of a patient or subject. Additionally or alternatively, the first preferred method S100 can estimate an extravascular blood volume that includes blood within the body of a patient or subject but external the vascular system of the patient.

The physical sample is preferably an absorbent surgical gauze sponge, a surgical dressing, or a surgical towel, though the sample can be any other textile. Additionally or alternatively, the physical sample can be a piece of clothing, a ground, table, wall, or floor surface, an external skin surface, a surgical glove, a surgical implement, or any other surface, material, substrate, or object. A surgeon, nurse, anesthesiologist, gynecologist, soldier, paramedic, or other user can use a machine or device incorporating the first preferred method S100 to estimate blood volume in one or more physical samples to generate a total estimated blood loss (EBL) of a patient, such as during a surgery, childbirth or any other medical or health-related event. Alternatively, a law enforcement officer, forensic investigator, or other user can use a machine or device implementing the first preferred method S100 to estimate extracorporeal blood volume at a crime scene or to assess victim risk during a medical emergency.

The first preferred method S100 can additionally or alternatively function to estimate the volume, mass, or quantity of another blood-related parameter or extracorporeal blood volume indicator in the physical sample, such as hemoglobin or red blood cell mass or volume in the physical sample. Such blood-related parameters can then be evaluated against additional variables or features to calculate the volume of blood, hemoglobin, red blood cells, white blood cells, plasma, etc. in the physical sample. For example, an estimated or measured hematocrit (HCT) of the blood of a patient can be used to estimate blood volume in the sample according to the formulas:

$$HCT = \frac{RBC}{EBL} = \frac{RBC}{RBC+PV}$$
$$HGB = .35 \times RBC$$

wherein RBC (red blood cell content) is substantially correlated with hemoglobin volume, PV is plasma volume, and EBL is estimated blood loss (or volume of blood in the physical sample) and is a composite of RBC and PV. The first preferred method S100 can additionally or alternatively function to detect presence of blood in the sample, compute blood spread rate, compute blood loss rate, calculate blood surface area, estimate patient risk level (e.g., hypovolemic shock), and/or determine hemorrhage classification of the patient. However, the first preferred method S100 can provide any other functionality, analyze any other image type or format, estimate any other blood-related parameter, and/or calculate blood volume in the physical sample in any other way.

Figure 9:
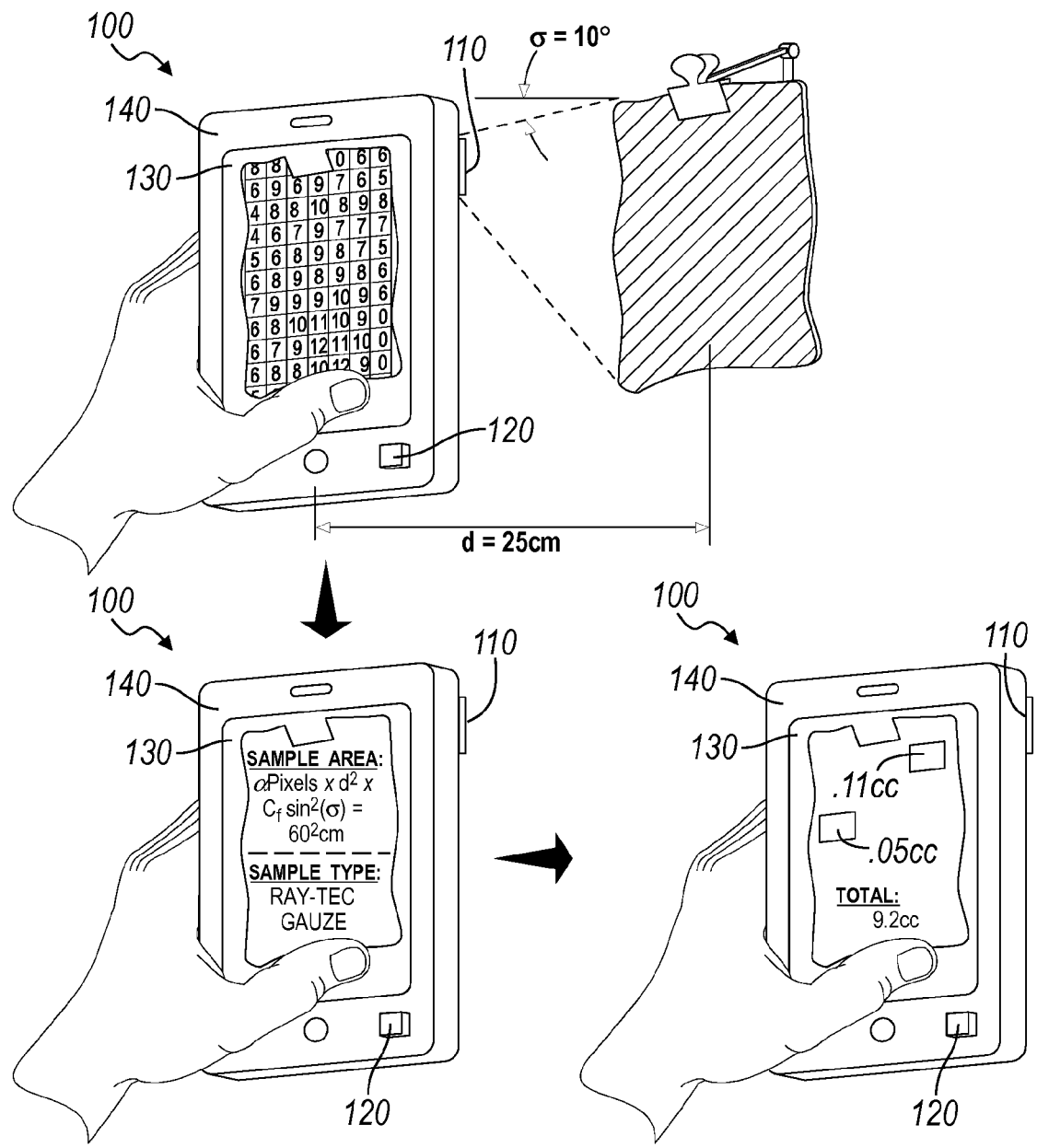
FIG. 9 is a schematic of a variation of the preferred system.

The first preferred method S100 is preferably implemented in a handheld (mobile) electronic device, such as an application (or 'app') executing on a digital music player, a smartphone, or a tablet computer, as shown in FIG. 9, wherein a camera integral with the electronic device captures the image of the sample, wherein a processor integral with the electronic device performs Blocks S110, S120, and S130, and wherein a display integral with the electronic device performs Block S160, which recites displaying the estimated blood volume of the portion of the physical sample, the whole of the physical sample, and/or a summed total blood volume across multiple physical samples. In this implementation, the electronic device can alternatively communicate with a remote server, such as via a wireless communication module 150 implementing cellular, Wi-Fi, or Bluetooth protocol, wherein the server performs at least some of Blocks S110, S120, and S130, and wherein at least some of the outputs of Blocks S110, S120, and S130 are transmitted back to the electronic device and subsequently displayed. However, the first preferred method S100 can also be a standalone blood volume estimation system, such as a system including a staging tray configured to support a sample, a camera configured to image the sample, and a processor configured to perform at least a portion of the first preferred method S100 and/or a communication module that communicates with a remote server configured to perform at least a portion of the first preferred method S100. However, the first preferred method S100 can be implemented in any other system, device, or combination thereof.

The first preferred method S100 can therefore be useful in a hospital setting, such as in a surgical operating room, in a clinical setting, such as in a delivery room, in a military setting, such as on a battlefield, in a law enforcement setting, such as at a crime scene, or in a residential setting, such as to monitor blood loss due to menorrhagia (heavy menstrual bleeding) or epistaxis (nosebleeds). However, the first preferred method S100 can be useful in any other setting.

Figure 1B:
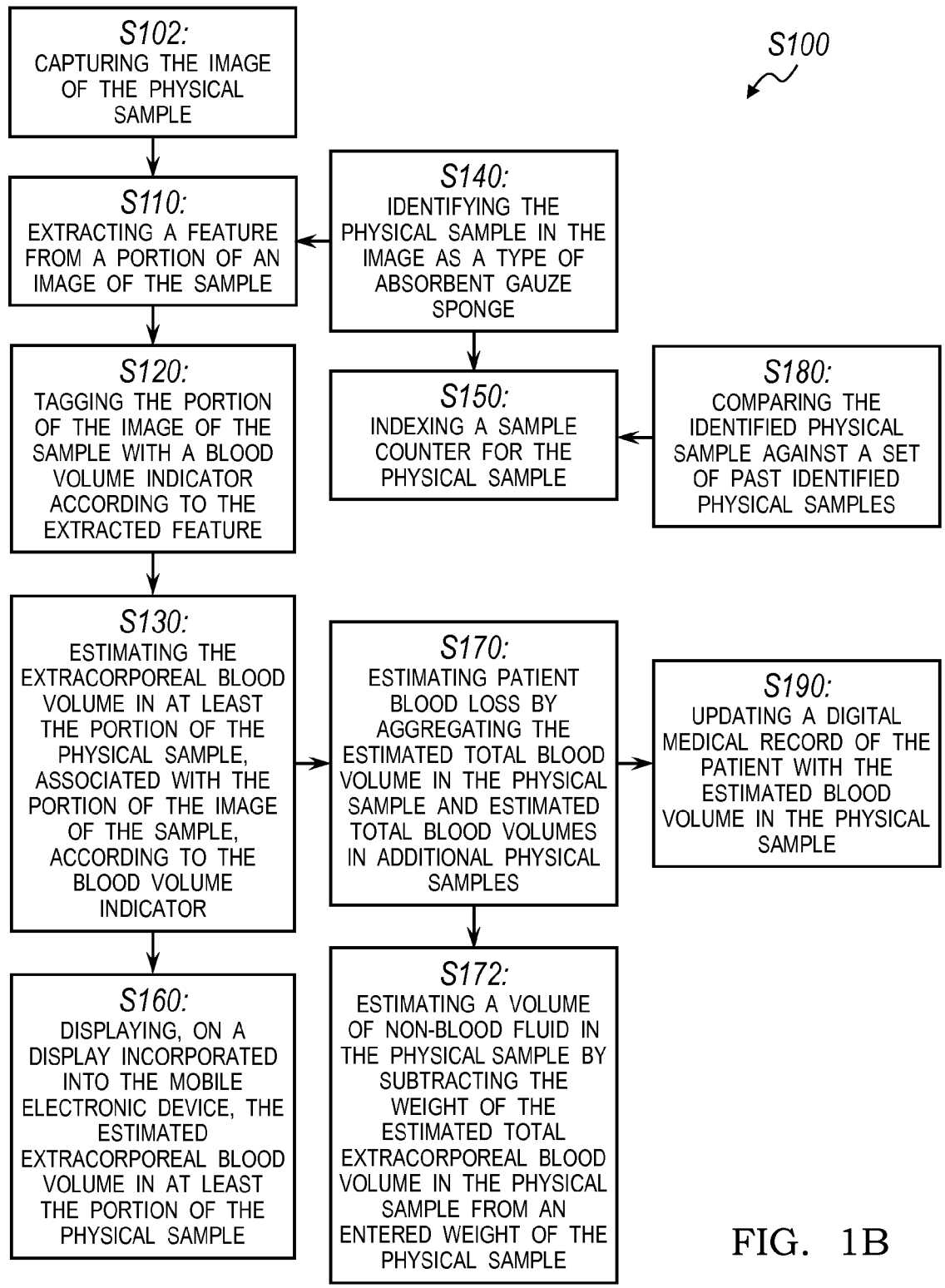
FIG. 1B is a flowchart representation of one variation of the first preferred method.
Figure 2A:
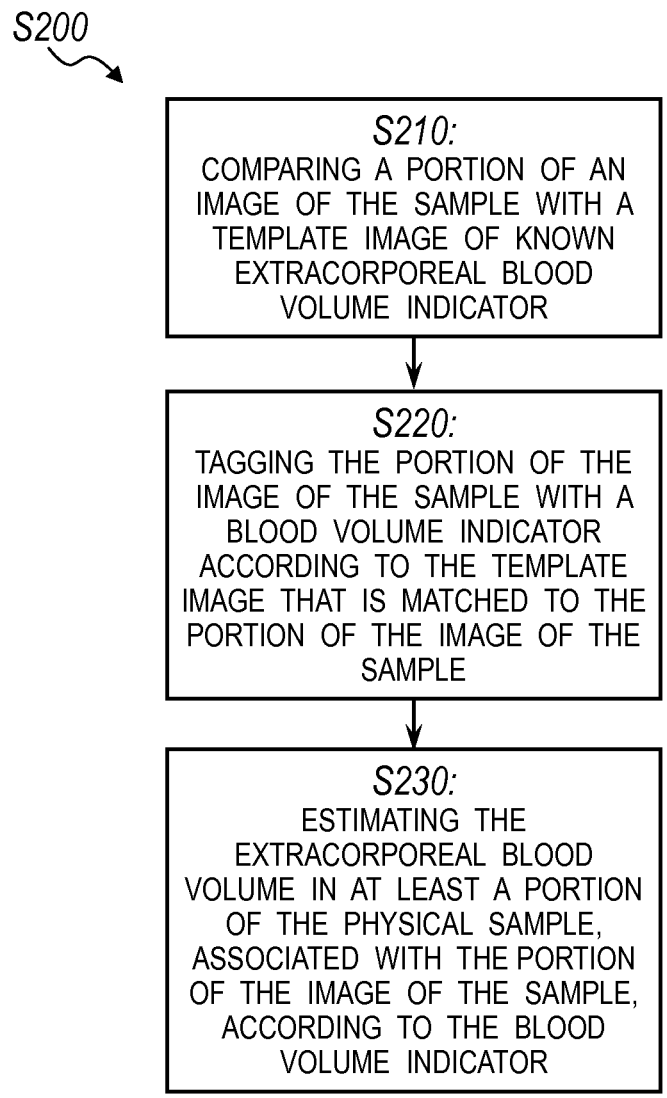
FIG. 2A is a flowchart representation of a method of a second preferred embodiment.
Figure 2B:
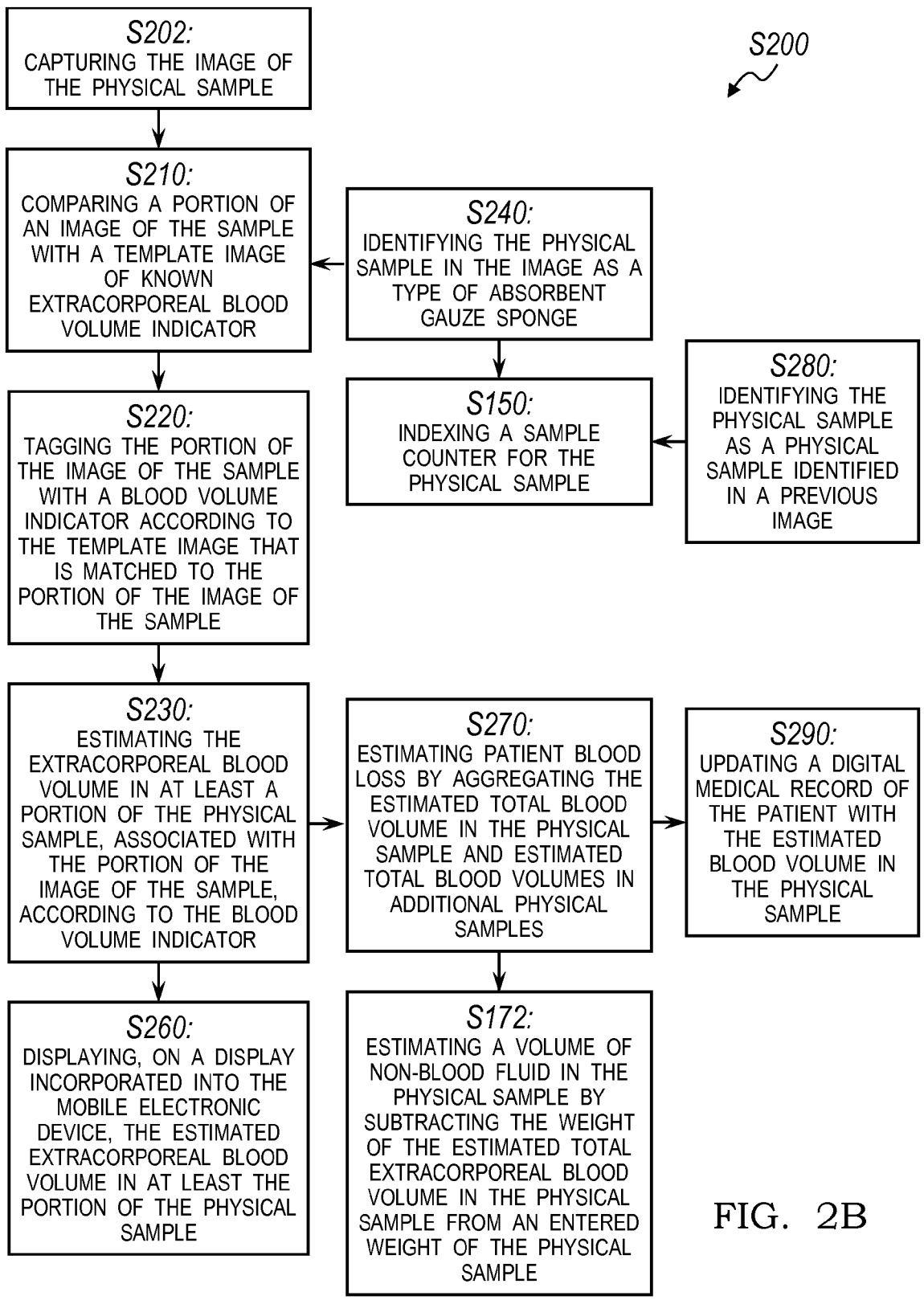
FIG. 2B is a flowchart representation of one variation of the second preferred method.

As shown in FIGS. 1, 2, and 3, Block S110 of the first preferred method S100 includes extracting a feature from a portion of an image of the sample. The extracted feature of the portion of the image preferably enables correlation (or pairing) of the portion of the image with a blood loss indicator of the portion of the sample in Block S120, which can further enable estimation of the blood volume in the portion of the sample in Block S130. The extracted feature is preferably an intensity, luminosity, hue, saturation, brightness, gloss, or other color-related value of the portion of the image in at least one component space, such as the red, blue, green, cyan, magenta, yellow, key, and/or Lab component spaces. Furthermore, the extracted feature can be a histogram of various color values across a set of pixels in the portion of the image. Additionally or alternatively, the extracted feature can be an estimated surface area of the sample shown in the image, an estimated surface area of a bloodied portion of the sample, a pixel count of the portion of the sample, a pixel count of the entire sample, or a pixel count of only the bloodied region of the sample, a color intensity value of an unsoiled portion of the sample, or any other relevant feature inherent in or available for extraction from the portion of the image of the sample. Furthermore, Block S110 can include extracting any number of features from all or a portion of the image of the sample.

Block S110 can similarly include accessing non-image features, such as a current patient intravascular hematocrit, an estimated patient intravascular hematocrit, an historic patient intravascular hematocrit, a weight of the sample, a clinician-estimated sample blood volume, computer-vision-based or gravimetric or human-generated estimates of blood volumes of previous samples, an ambient lighting condition, a type or other identifier of the physical sample, properties of the physical sample, a patient vital sign, patient medical history, an identity of a surgeon, or a type of surgery. Any of these non-image features can inform selection of template images for comparison with the portion of the sample image, selection of a particular parametric model or function, definition of alarm triggers for misplaced surgical gauze sponges, definition of alarm triggers for excess fluid or blood loss, transformation of extracted features into the blood volume indicator, and/or estimation of blood volume from the blood volume indicator. However, any of these non-image features can modify enable, or inform any other function of the first preferred method S100.

Figure 4:
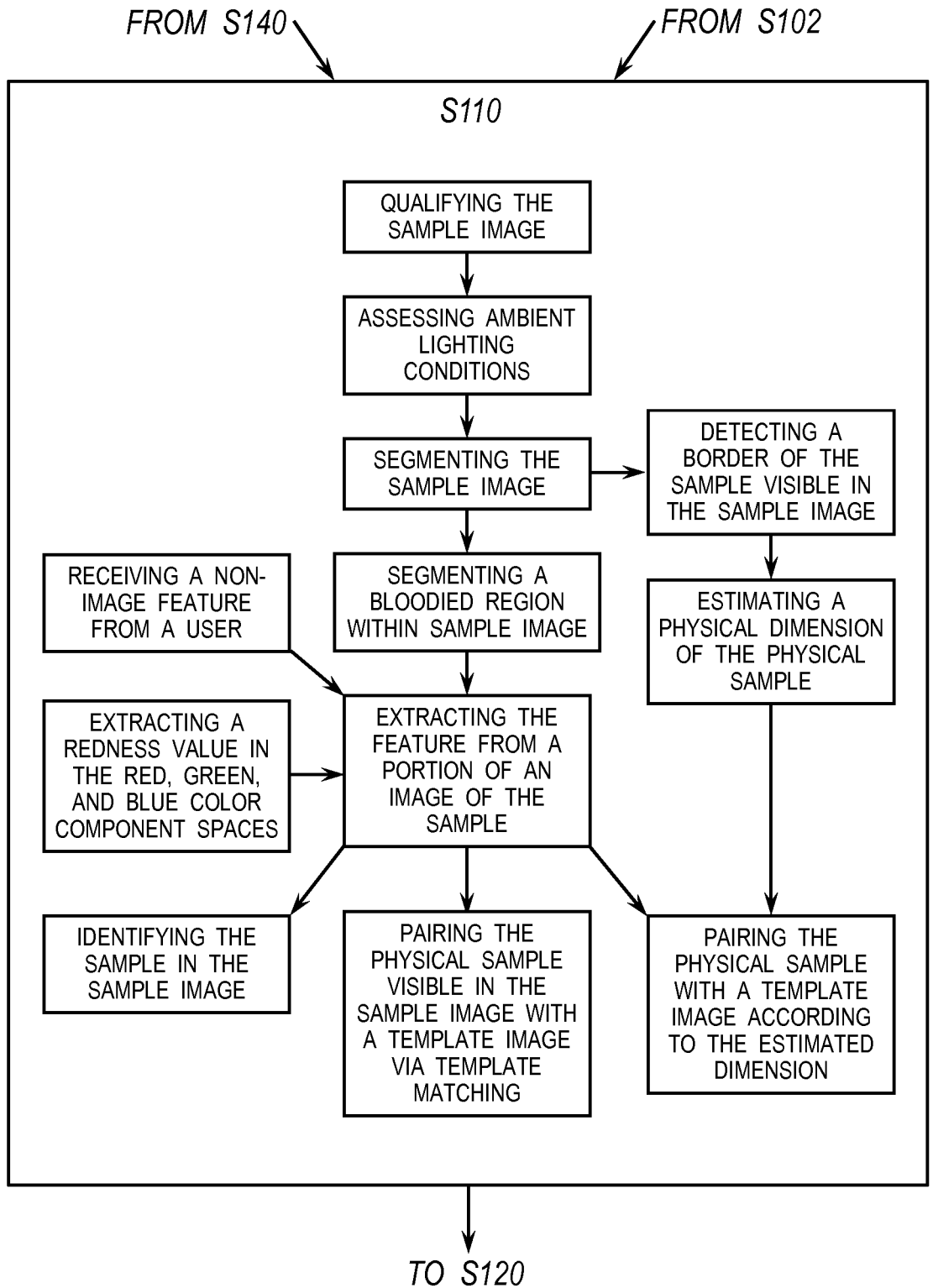
FIG. 4 is a flowchart representation of one variation of the first preferred method.

As shown in FIG. 4, Block S110 preferably includes segmenting the image, including isolating a first segment of the sample image representative of the physical sample that is a bloodied object (e.g., a surgical gauze sponge). Block S110 preferably subsequently further segments the first region to define the portion of the sample image that corresponds to a particular portion of the physical sample captured in the sample image. Segmenting the sample image into multiple image segments preferably increases the resolution and/or accuracy of the estimated blood volume of each portion of the physical sample. The size and shape of each image segment can be static, wherein each segment comprises a predefined number of pixels in the image and/or a predefined dimension in physical space, as shown in FIG. 9. For example, the image segment can define a ten-pixel by ten-pixel rectilinear area of the image or a five-millimeter equilateral triangular area of the physical sample. In another variation, the image segment can be isolated according to properties of individual pixels or groups of pixels in the image, such as hue, saturation, shade, brightness, chroma, wavelength, or any other metric of color or light, as shown in FIG. 7. In this alternative, the sample image can be dynamically segmented, wherein portions of the sample image are separated by color property or other features rather than by (or in addition to) pixel location or by location on the physical sample. However, the portion of the sample image can include the whole of the physical sample associated with the sample image, or the sample image can be segmented or apportioned according to any other schema. The portion of the sample image is preferably a single segment or region including multiple pixels of the image, but the portion of the sample image can alternatively be a plurality of image segments or regions of the sample image, can be of any other size, and/or can be of any other form.

In a variation of the first preferred method S100, Block S110 extracts a feature from the sample image that is a dimension of the physical sample. In one example implementation, Block S110 implements object recognition to isolate an object of known type within the field of view of the optical sensor and/or within the sample image. The object can be a surgical tool, a surgical tray, an operating table, a surgical gauze sponge, a suction canister, or any other object of known dimension. From this known dimension, a dimension of the physical sample can be extrapolated, such as by estimating the distance from and/or angle between the optical sensor and the known object and comparing the position of the sample and the known object in the image. In another example implementation, Block S110 analyzes shadows in the sample image, coupled with known locations of light sources, to estimate an angle and distance between the physical sample and the capture origin (i.e. the location of the camera or optical sensor when the sample image was captured). In yet another example implementation, the optical sensor is arranged at a known distance from and angle to a staging tray on which the physical sample is arranged for imaging, and Block S110 includes extrapolating the dimension of the physical sample or a portion therefore based upon known placement of the optical sensor relative the staging tray. A further example implementation, Block S110 manipulates an IR, sonic, laser, or other type of distance sensor arranged adjacent the optical sensor to transmit a signal toward the physical sample to determine the distance and/or angle between the physical sample and the capture origin of the image. However, a dimension of the physical sample or a portion thereof can be estimated or determined in any other way.

In the foregoing example implementations, the distance and/or angle between the sample and the optical sensor can be automatically extracted from the image to inform a transform from pixel count of the portion of the sample image into a physical dimension (e.g., inch, centimeter) of the corresponding portion of the physical sample in Block S110. The estimated angle and/or distance can therefore define an extracted feature of the sample image that informs the generation of the blood indicator tag and/or the transformation of the blood indicator tag into the estimated blood volume in the portion of the physical sample. However, the distance and/or angle value(s) can be input by a user (e.g., a surgeon, a nurse), extrapolated from data generated by a non-optical sensor, or calculated or gathered in any other way to define a non-image feature related to the sample.

Block S110 can additionally or alternatively implement any object localization, segmentation (e.g. using edge detection, background subtraction, graph-cut-based algorithms, etc.), gauging, clustering, pattern recognition, template matching (using any one of various metrics), feature extraction, descriptor extraction (e.g. extraction of texton maps, color histograms, HOG, SIFT, etc.), feature dimensionality reduction (e.g. PCA, K-Means, linear discriminant analysis, etc.), feature selection, thresholding, positioning, color analysis, parameteric regression, non-parametric regression, unsupervised or semisupervised parametric or non-parametric regression, or any other type of machine learning or machine vision to estimate a physical dimension of the sample. Such methods preferably compensate for varying lighting conditions of the physical sample, warping of the physical sample (e.g., a wrinkle or warped gauze sponge), warping of the image of the physical sample (e.g., due to optical distortion caused by a lens of the optical sensor), variations in composition of the fluid present in or on the sample, or any other inconsistency or variable prevalent in any use scenarios. For example, once the object, materials, gauze type, etc. of the physical sample is identified, the estimated surface area of the physical sample can be compared with a known surface area of a template sample of the same object, material, or gauze type to correct for area estimation errors, such as due to a wrinkle or other non-uniformity in the physical sample when the sample image was taken.

In another variation of the first preferred method S100 and as shown in FIG. 4, Block S110 includes assessing ambient lighting conditions, wherein the ambient lighting conditions define an extracted feature. For example, the 'redness,' 'greenness,' and 'blueness' values (i.e. color values in the red, green, and blue color component spaces) of pixels of bloodied regions in the sample image can be combined into a weighted composite color value according to ambient lighting conditions proximal the sample when the sample image was captured. In this example, the weighted composite color value can then be fed into a parametric function or compared against color values of template images to generate the blood volume indicator.

In one variation of the first preferred method S100 shown in FIG. 4, Block S110 includes extracting a feature that identifies the physical sample in the sample image as an absorbent surgical gauze sponge. In this variation, Block S110 preferably implements machine vision, such as object segmentation, edge detection, pattern recognition, or template matching, to determine if the sample image includes an absorbent surgical gauze sponge or if an absorbent surgical gauze sponge is within a field of view of a camera or other optical sensor. Furthermore, Block S110 can preferably determine the type of absorbent surgical gauze sponge, such as laparotomy or RAY-TEC gauze, which can inform selection of a template image of a similar template sample type for comparison with the portion of the sample. Block S110 can additionally or alternatively identify thread count, external dimension, color, physical tag, or any other identifying feature or property of the physical sample to identify the type of sample or a fluid absorptivity, saturation volume, dry weight or mass, dry color, or any other property of the physical sample. Block S110 can therefore reduce processing time necessary to return a template image match for the portion of the sample by isolating key identifying features of the physical sample. Similarly, Block S110 can improve accuracy of the blood volume estimation by isolating key properties that affect fluid absorbance and a correlation between fluid volume and optical properties of the physical sample.

Block S110 can additionally or alternatively extract features from the sample image that identify other relevant objects, materials, or fluids in the sample image and/or the field of view of the optical sensor. For example, Block S110 can recognize drops, pools, or smears of blood on a surgical tool, tray, table, wall, floor, or other surface as containing blood. Block S110 can initiate an estimation of blood volume in or on a sample that is other than an absorbent surgical gauze sponge, surgical dressing, or surgical towel. In this variation, template matching can be used to estimate blood volume in or on the physical sample, as described below, although color value, translucency, saturation, dimension, or any other metric of the sample can be used to parametrically or non-parametrically generate the blood volume indicator tag and/or estimate the extracorporeal blood volume in at least the portion of the physical sample.

As shown in FIGS. 1, 2, and 4, Block S120 of the first preferred method S100 includes tagging the portion of the image of the sample with the blood volume indicator according to the extracted feature. The extracorporeal blood volume indicator tag is preferably an intermediate parameter for a region of interest in the sample image that translates pixel-level data in the sample image into a blood volume-related variable. The blood volume indicator tag is therefore preferably an estimate of hemoglobin content (e.g., mass, volume, density, percentage by weight, etc.) in the portion of the sample, though the extracorporeal blood volume indicator tag can alternatively be an estimate of red blood cell count or content, white blood count or content, platelet count or content, plasma content, or any other suitable extracorporeal blood volume indicator. The tag can also include any other relevant information, such as estimated hematocrit of the blood in the portion of the physical sample, a time stamp of when the sample image was taken, a time stamp of when the sample image was analyzed, or volume or concentration of other fluids present on or in the portion of the sample, such as bile, saliva, gastric fluid, mucus, pleural fluid, saline, or fecal matter. Generally, the blood volume tag is preferably of a form that can be transformed or manipulated into an estimated extracorporeal blood volume in all or a portion of the sample. Furthermore, the extracorporeal blood volume indicator tag for the portion of the sample image is preferably stored with the portion of the sample image or as a pointer to the portion of the sample image.

In one variation of the first preferred method S100, Block S120 includes comparing the extracted feature of the portion of the image of the sample against similar features extracted from template samples (e.g., a training set, samples analyzed previously) of known blood volume indicators and/or known extracorporeal blood volumes. In this variation, the portion of the image is tagged with the blood volume indicator based upon a non-parametric correlation with one or more template samples. For example, in this variation of the first preferred method S100, Block S120 can include implementing a K-nearest neighbor method to compare the extracted feature of the image that is a redness intensity in the red component space with redness intensity values of template samples. In this example, Block S120 can further include implementing a K-nearest neighbor method to compare extracted features that include a greenness intensity and a blueness intensity (in conjunction with a redness intensity) of pixels from bloodied regions in the sample image with greenness and blueness intensity values of template samples.

In one example implementation of this variation of the first preferred method S100, Block S120 includes pairing the portion of the image of the sample to a template image of known extracorporeal blood volume indicator. Each template image is preferably contained within a library of template images, and each template image is preferably an image of a template sample of known blood, hemoglobin, red blood cell mass or volume (e.g., per unit physical area), and/or any other suitable blood-related parameter, blood volume indicator, or feature. Each template image in the library is preferably tagged with an extracorporeal blood volume indicator such that the portion of the sample image can be matched to a template image in Block S110, and such that a tag, indicative of the blood volume in the portion of the physical sample, can be associated with the portion of the sample image in Block S120.

The library of template images can be assembled in a variety of ways. In one example, an image is taken of a template sample that is a used surgical gauze, blood is washed from the used gauze and assayed to determine the hemoglobin mass absorbed into the used gauze, the image of the template sample is tagged with the hemoglobin mass (the extracorporeal blood volume indicator), and the image is catalogued in the library. In another example, a template sample is prepared by adding a known volume of blood (of known hematocrit) to a surgical gauze of a known size, an image of the template sample is taken, the image of the template sample is tagged with the known blood volume (the extracorporeal blood volume indicator), and the image is catalogued in the library. The blood volume tag of each image template is preferably a volume or mass of a blood-related parameter, such as hemoglobin or red blood cell content per physical area (e.g., 1 $cm^2$) such that, in Block S130, a blood volume indicator tag of a portion of the image can be multiple by an estimate physical area (or volume) of the corresponding portion of the physical sample to estimate the extracorporeal blood volume in the portion of the sample, as shown in FIG. 7. However, the template sample for each template image can be prepared in any other way or combination of ways, and the extracorporeal blood volume indicator can be any other suitable parameter or metric. The library preferably contains a large number of template images to account for variance in lighting, image quality, type of physical sample (e.g., type of surgical gauze sponge), volumes, concentrations, or hematocrits of blood or other indicator in each sample, "age" of the physical sample, surgical conditions, or any other suitable variable. Furthermore, the template images in the library can also be grouped, such as according to: the type of template sample, such as a gauze sponge, floor, operating table, clothing; lighting or backlighting of the template sample; hematocrit of blood in a template sample; thread count of the template sample that is a textile; quality of the image of the template sample, such as depth of field, focus, distance between the template sample and an optical sensor; or any other suitable parameter. The library can be stored locally on a machine or system configured to perform at least a portion of the first preferred method S100, or remotely, such as on a remote server or hard drive accessible by the machine or system when performing at least a portion of the first preferred method S100.

In this example implementation, the sample image can be compared directly to the template image via template matching in Block S120. In Block S110, each image segment can be decomposed into features that are separate color components (e.g., red, green, and blue), and the absolute difference in pixel intensity for the pixels in the portion of the sample image and the pixels in the template image can be calculated for at least one color component. (However, the sample image can alternatively be decomposed prior to segmentation.) In this example implementation, the absolute difference in pixel intensity is preferably calculated at a wavelength of light that correlates with the extracorporeal blood volume indicator. For example, the absolute difference in pixel intensity for the portion of the sample image and the template image can be calculated at 400 nm, a wavelength that can correlate well with hemoglobin concentration for certain absorbent surgical gauze sponges. The template image is preferably paired with the portion of the image when a substantially minimal sum of absolute difference in pixel intensity between the portion of the sample image and the template image is calculated.

Alternatively, Block S120 can implement a texton map to pair the sample image with one or more template images. In this implementation, to build the template image library patches from template (training) images can be clustered into centroid patches, such as by k-means clustering. For each pixel or set of pixels in each training image, the index of the centroid patch nearest the patch surrounding the pixel can be calculated such that a histogram, of the nearest-centroid indices within a window around each pixel, can be constructed. By averaging the histograms of all background pixels, a background histogram centroid can also be constructed. Clean and bloodied histogram centroids for physical samples (e.g., surgical gauze sponges) can be similarly constructed. Alternatively, a classification algorithm such as SVM, Naïve Bayes, LDA, K-Nearest-Neighbors, or logistic regression, can be trained using histograms centered around or mostly containing background, bloodied, and unsoiled pixels. When the portion of the sample image is compared with template images in the template image library, histogram of the nearest-patch-centroid indices around each pixel in the portion of the sample image is generated and classified based upon a comparison of the histogram and histogram centroid of the pixel, or based upon the output of one of the learned classifiers described above. The histograms and/or histogram centroids of the pixels in the portion of the sample image can then be compared with a subset of histograms and/or histogram centroids of pixels of the template images, based upon the determined class of physical sample, to pair one or more template images with the sample image.

In this example implementation, Block S120 therefore preferably recites stepping through subsequent template images in the template image library until a suitable match is found for the portion of the sample image. However, the hue, saturation, shade, brightness, chroma, intensity of wavelength, wavelength range, histogram, histogram centroid, class, or any other color property (e.g., feature) of the portion of the sample image and the template image can be compared in Block S120. In this example implementation, the portion of the sample image and the template image are preferably compared substantially directly. However, the template image and the portion of the sample image can be compared via template matching incorporating any other vision algorithm or image processing method.

In another example implementation of this variation of the first preferred method S100, each template image is a different color or hue in a library of color palettes, wherein each color correlates with a different blood volume or blood volume indicator. In this example implementation, the library preferably includes color palettes for different types of surgical sponge gauzes, surgical towels, surgical tool surfaces, floor surfaces, operating or delivery table surfaces, and/or any other common surface, material, object, or feature, wherein each color that is a template image in a color palette is associated with a particular red blood cell content or indicator for a particular type of physical sample. In this example implementation, the template image that is a color can be an image of the color or a numerical color identifier, such as a HEX code value (e.g., #FF0000, #A00000, #880000, etc.) or an RGB code value (e.g., (255, 0, 0), (160, 0, 0), (190, 0, 0), etc.).

In yet another example implementation of this variation of the first preferred method S100, the feature extracted from the portion of the sample image in Block S110 is a redness value, wherein the redness value is an intensity of a wavelength or composite intensity of a range of wavelengths of light, redness hue, redness saturation, or any other suitable light- or color-related value. Block S110 can similarly extract greenness, blueness, or other color component values of one or more bloodied pixels in the sample image. Generally, Block S110 preferably decomposes the sample image into distinct color spaces, such as red, green, and blue component spaces, wherein a color value or intensity is calculated for the portion of the sample image in each color space. Furthermore, the portion of the sample image that is decomposed in Block S110 preferably includes red pixels indicative of blood content in the portion of the physical sample that is associated with the portion of the sample image. In Block S120, the color value(s) of the portion of the image are then compared substantially directly with color values of template images until a suitable match is found.

In this variation of the first preferred method S100, template images with properties substantially dissimilar from those of the portion of the physical sample or the sample image can be withdrawn from comparison with the portion of the sample image in Block S120 in order to reduce processing time required to find a template image match. In one example implementation, template images of template samples of surfaces, products, materials, or dimensions substantially dissimilar from that of the portion of the physical sample are excluded from comparison. For example, Block S110 can extract a thread count feature from the sample image, wherein the thread count feature identifies the physical sample as laparotomy gauze, and wherein all template images of template samples that are not of laparotomy gauzes are removed from comparison with the portion of the sample image. In another variation, thresholding is used to remove substantially irrelevant template images from the test pool. In one example, template images with redness values (e.g., intensity, hue, saturation, shade, brightness, chroma, wavelength range) substantially dissimilar from that of the portion of the sample image are excluded from comparison. Tree search can additionally or alternatively be used to reduce processing time. However, template images can be grouped in the template library and selected or deselected for comparison with the portion of the sample image according to any other schema.

In another variation of the first preferred method S100, Block S120 includes transforming the extracted feature of the portion of the image of the sample into the blood volume indicator. In this variation of the first preferred method S100, Block S120 preferably implements an algorithm or other mathematical transformation to convert the extracted feature into the blood volume indicator for the portion of the image of the sample. Therefore, in this variation, Block S120 preferably implements parameterized generation of the blood volume indicator.

In one example implementation, color values of the template images are used to generate a mathematical function, curve, or algorithm that correlates the extracted feature to the blood volume indicator. Generally, the extracted feature of the portion of the sample image (e.g., redness intensity in the red component space, blueness intensity in the blue component space, greenness intensity in the green component space, or a composite of two or three color intensities) can be plugged into a parametric function (e.g., intensity-blood volume function) to directly calculate the blood volume indicator, from the extracted feature, for the portion of the sample image. For example, reflectance of oxygenated hemoglobin ($Hb_{O2}$) can be correlated with certain wavelengths of light to substantially directly estimate the content of hemoglobin in the portion of the physical sample associated with the portion of the image. In this example, because the hemoglobin content of a wet (hydrated) red blood cell is typically about 35%, red blood cell count can be extrapolated from hemoglobin content.

Blocks S120 and S130 can implement both parametric and non-parametric techniques or methods to correlate one of more extracted features to one or more blood volume indicators. For example, extracted features that are color values in the red, green, and blue color spaces can be compared with template images via non-parametric techniques (e.g., template matching) to tag the portion of the sample with the blood volume indicator, and an extracted feature that is an estimated surface area of a bloodied region of the physical sample can be transformed according to a parametric function to generate a coefficient for conversion of the blood volume indicator into an estimated blood volume in the portion of the sample. In this example, another extracted feature that is the type of physical sample (e.g., laparotomy gauze, RAY-TEC gauze, surgical table, floor, article of clothing) functions to qualify the sample to inform selection of template images for comparison with the portion of the sample image. However, Block S120 and S130 can manipulate any relevant image-based feature extracted in Block S110 or any non-image-based feature (e.g., sourced from a clinician, sourced from a medical record, etc.) to generate the blood volume indicator of the portion of the image and the estimated blood volume for at least the portion of the sample, respectively.

Figure 5:
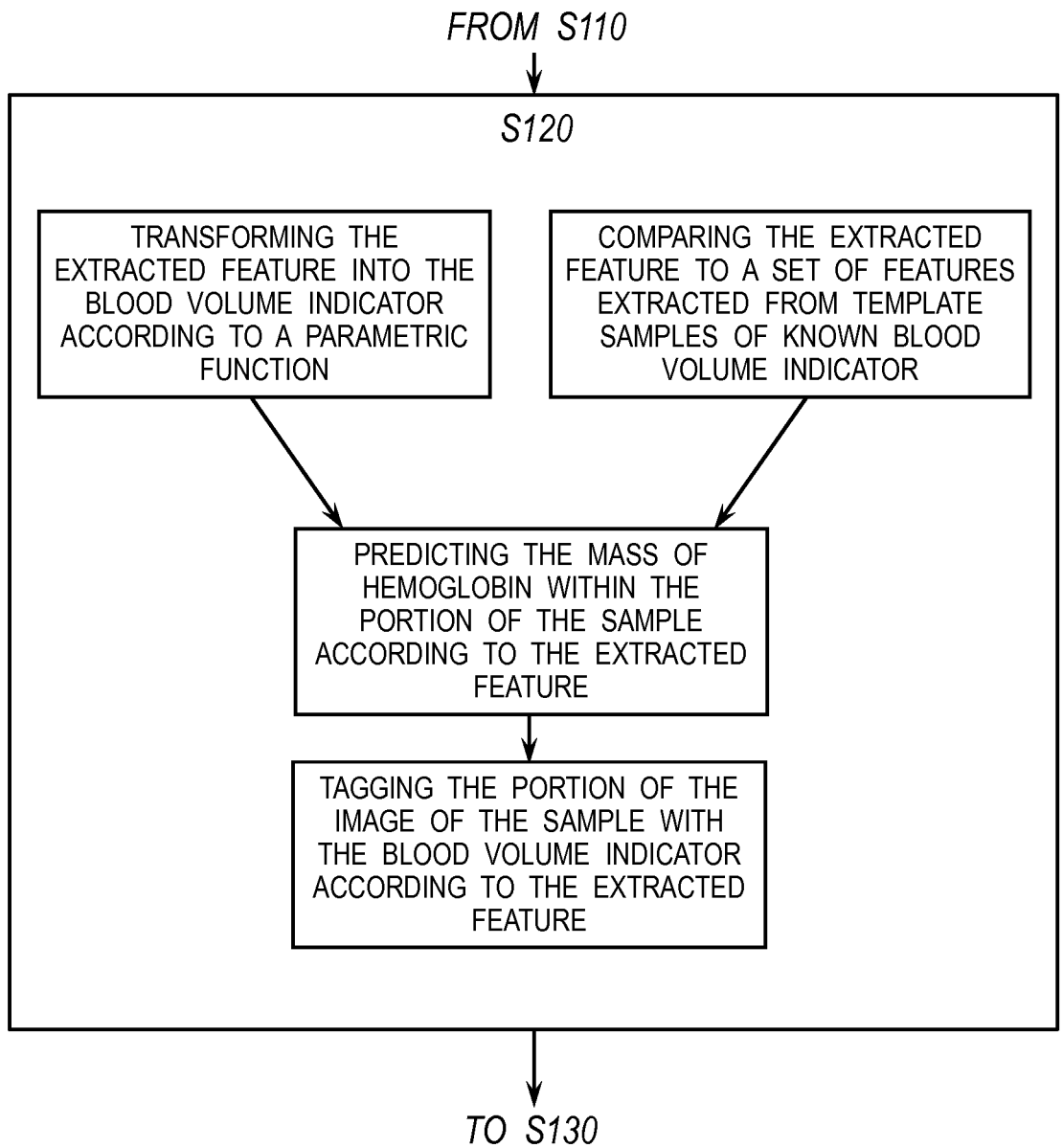
FIG. 5 is a flowchart representation of one variation of the first preferred method.
Figure 6:
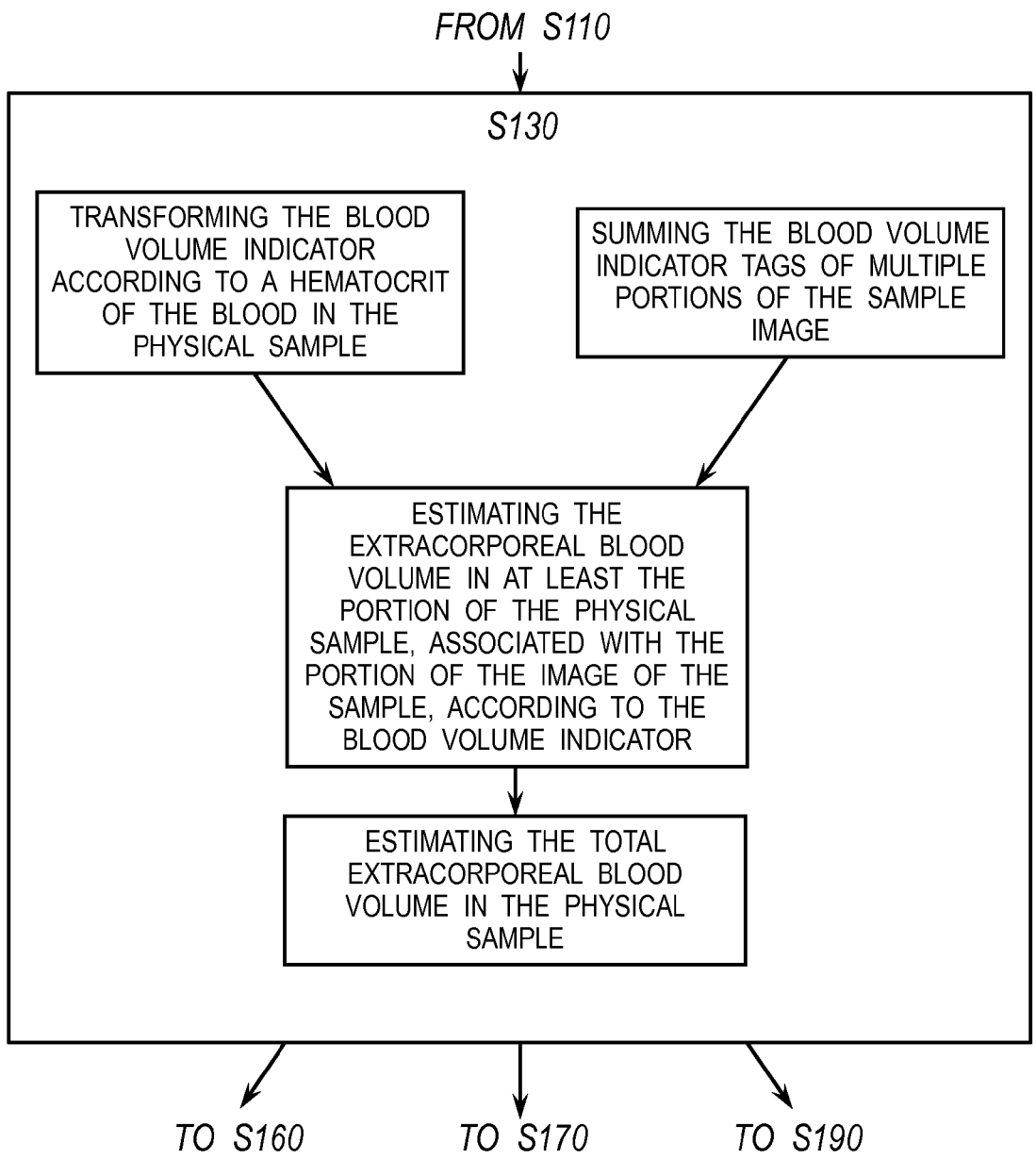
FIG. 6 is a flowchart representation of one variation of the first preferred method.

As shown in FIGS. 1 and 5, Block S130 of the first preferred method S100 includes estimating the extracorporeal blood volume in at least a portion of the physical sample, associated with the portion of the sample image, according to the blood volume indicator tag. For example and as described above, the blood volume indicator tag that is a hemoglobin content can estimate red blood cell volume through the formulas $$RBC=HGB/0.35 \text{ or}$$

$$HCT=3\times HGB,$$

which in turn can be used to predict blood volume. The blood volume for each portion of the physical sample correlating with a portion of the image can be independently calculated and then summed to estimate a total blood volume in the physical sample. Alternatively, the blood volume indicator tags for substantially all portions of the image can be summed and/or averaged and the total blood volume in the physical sample calculated at once. The estimated blood volumes across multiple samples can then be summed to generate a total blood volume in the samples, which preferably correlates with a total estimated blood loss of a patient. However, Block S130 can additionally or alternatively include estimating total hemoglobin mass or volume, total red blood cell mass or volume, or any other blood-related metric in the physical sample or across multiple samples.

As shown in FIG. 1B, a variation of the first preferred method S100 further includes Block S140, which recites identifying the physical sample in the image as a type of absorbent gauze sponge. Block S140 preferably implements machine vision techniques to determine the type of physical sample, as described above. From identification of the type of physical sample in Block S140, the first preferred method S100 can access sample-specific data such as dry weight, absorptivity, fluid saturation volume, or any other data or property of the physical sample, which can enable extraction of additional blood-related data from the image of the physical sample.

As shown in FIG. 1B, another variation of the first preferred method S100 can further include Block S150, which recites indexing a sample count for the physical sample. The sample count is preferably a count of absorbent surgical gauze sponges, dressings, or towels, though the sample count can additionally or alternatively be a count of blood droplets, blood drops, pools of blood, bloodied articles of clothing, bloodied surgical tools, or any other relevant or suitable blood formation or bloodied object. The sample count is preferably displayed with the estimated blood volume of the portion of the physical sample, and the sample count is preferably indexed substantially in real time when the image of the physical sample is taken. However, Block S150 can function in any other way to index the sample count and to provide this information to a user.

As shown in FIG. 1B, another variation of the first preferred method S100 further includes Block S160, which recites displaying the estimated blood volume in the portion of the physical sample, the estimated blood volume in the whole physical sample, and/or the estimated total blood volume across multiple physical samples. At least some of this data is preferably presented to a user, such as to a surgeon, a nurse, an anesthesiologist, a gynecologist, a doctor, or a soldier. This data is preferably rendered on a digital display of a machine or system configured to perform at least a portion of the first preferred method S100. As shown in FIG. 9, this data can be presented in the form of an augmented reality overlay on top of the static sample image depicted on the display. Alternatively, this data can be presented in the form of a dynamic augmented reality overlay on top of a live video stream captured by the optical sensor and depicted on the display. For example, data can be presented in an augmented reality overlay on subsequent scanned images of one physical sample, wherein the camera captures digital images at a rate such as 30 frames per second and the augmented reality overlay updates with each new frame or number of frames. This data can alternatively be presented in table, chart, or diagram including the estimated blood volume in one or more physical samples over a period of time. Other blood-related metrics can also be estimated or maintained in the first preferred method S100 and presented in Block S160, such as blood spread rate, blood surface area, patient risk level, or patient hemorrhage classification. However, this data or any other blood-related metric or patient information can be presented in any other way or form in Block S160.

Figure 10:
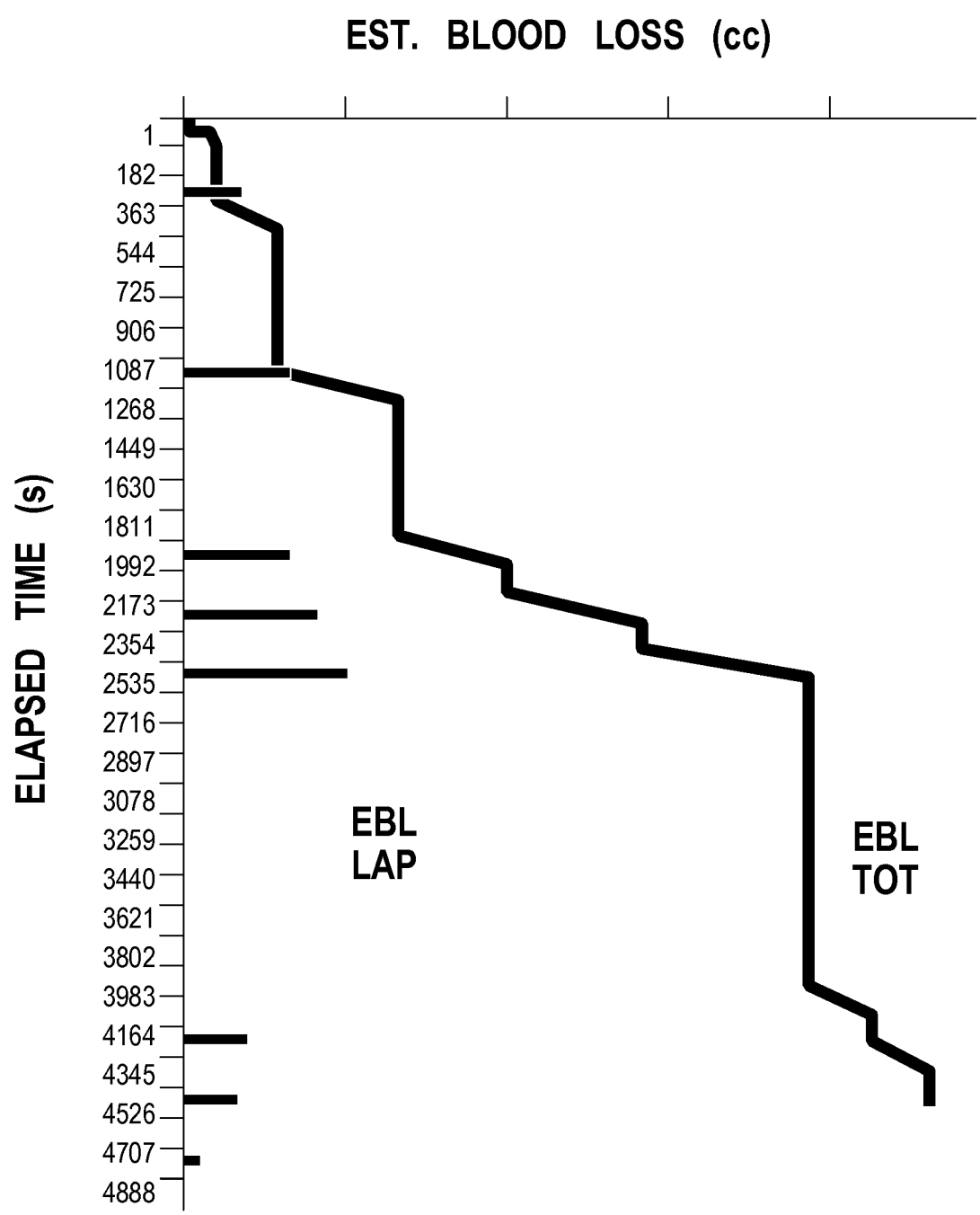
FIG. 10 is a graphical representation of an output in accordance with a system or a method of a preferred embodiment.

As shown in FIG. 1B, another variation of the first preferred method S100 further includes Block S170, which recites estimating patient blood loss by summing the blood volume estimate of the physical sample with previous blood volume estimates of other physical samples. Additionally or alternatively, the blood volume estimate of the physical sample can be stored for future summation with blood volume estimates of additional physical samples. By summing blood volume estimates across multiple physical samples, blood loss of a patient can be tracked over time. For example, during a surgery, used surgical gauze sponges can be analyzed via Blocks S110 and S120, wherein a running summation of blood volumes in each used gauze sponge provides time-elapse estimates of total blood loss of the patient, as shown in FIG. 10. This may be useful in estimating patient risk, in determining when to administer saline or provide a blood transfusion, in maintaining record of surgical events, and/or in estimating future blood-related events or patient needs. Other blood-related metrics can also be estimated or maintained in Block S130 and summed over time in Block S170.

As shown in FIG. 1B, another variation of the first preferred method S100 further includes Block S180, which recites comparing the identified physical sample against a set of past identified physical samples. In this variation, Block S150 preferably indexes the sample counter only when the identified physical sample is determined to be unique amongst the set of past identified physical samples. Block S180 therefore functions to determine if a previous sample image including the same physical sample was already analyzed according to any of Blocks S110, S120, and/or S130. Block S180 preferably substantially guards against double counting of the estimated blood volume in the physical sample in Block S170. Each sample image, a fingerprint of each sample image, or a fingerprint of each physical sample is therefore preferably stored, such as on a local or remote sample image database, such that subsequent sample images or physical samples can be compared against past sample images or physical samples in Block S180. In Block S180, comparison of the sample image with previous sample images can require scale, rotation, mirror, stretch or other transformations or fingerprinting of the sample image and/or or previous sample images. Edge detection, segmentation, pattern recognition, feature extraction, and/or other machine vision techniques can be used to determine the uniqueness of bloodied regions of the physical sample shown in the sample image, relative to bloodied regions of other, previously analyzed physical samples. However, Block S180 can function in any other way to identify the sample image as including the physical sample that was included in a previous sample image.

As shown in FIG. 1B, another variation of the first preferred method S100 further includes Block S190, which recites updating a digital medical record of the patient with the estimated blood volume in the physical sample. Block S190 can additionally or alternatively update the medical record of the patient with the estimated blood volume across multiple physical samples, the estimated blood loss of the patient, patient blood loss trends, or any other relevant metric or data generated related to the circulatory system of a patient. The digital medical record can be maintained locally on a machine or system implementing the first preferred method S100 or on a local network or remote server accessed by the machine or system to retrieve, update, and/or upload the digital medical record.

In a further variation of the first preferred method S100, the physical sample is a fluid canister that collects bodily fluids of a patient, such as blood, bile, saliva, gastric fluid, mucus, pleural fluid, urine, or fecal matter, wherein the image is an image of the fluid canister. In an example implementation of this variation, Block S110 can include extracting features that include a volume of fluid within the canister, as well as redness, greenness, and blueness intensities of the portion of the image of that canister that includes bloodied pixels and preferably includes little to no glare. Furthermore, Block S120 can include estimating a percentage of blood within the canister relative to other bodily fluids based upon the extracted color values, and Block S130 can include estimating the volume of blood within the canister. In this variation of the first preferred method S100, the optical sensor that captures the image of the fluid canister is preferably mounted to the fluid canister. In one example implementation, the optical sensor is mounted to the side of and facing the fluid canister that is cylindrical such that the fluid level in the fluid canister can be estimated directly from the sample image. In another example implementation, the optical sensor is mounted overhead the fluid canister that also includes a fluid level sensor, wherein an output of the fluid sensor defines a non-image feature that informs at least one of the blood volume indicator and the estimated blood volume in the fluid canister. Alternatively, the optical sensor can be incorporated into a handheld device, wherein a user scans the fluid canister with the optical sensor to capture the sample image. In addition, an auxiliary light source (such as a lamp or laser next to the canister) could be added to the system to enhance the correlation of color with concentration of hemoglobin or other substances. Alternatively or in addition, ambient light could be assessed and used as a feature.

Because fluid is added to the fluid canister over time, subsequent sample images of the fluid canister can be captured and analyzed over time, via the first preferred method S100, to generate a time-dependent, historical chronicle of fluid content of the fluid canister. Estimated blood volume in the fluid canister can therefore be monitored over time, such as to generate a trend in blood loss for a patient. Such data can be useful to trigger alarms if patient blood loss is occurring too rapidly or if patient blood loss has reached a critical total volume or critical red blood cell loss. However, loss of other fluids can also be monitored. For example, urine content (or total water content) of the fluid canister can enable tracking of patient hydration level such that the patient can be administered saline when hydration level or hydration loss surpasses a threshold. Differences between fluid color properties of one sample image at a first time and a subsequent sample image at a second time can indicate concentration changes of fluids in the fluid canister between the first and second times. Furthermore, a change in fluid level in the canister between the first and second times, coupled with fluid concentration changes, can indicate the floor rate of fluids into (or out of) the fluid canister. Estimated blood and/or other fluid loss through analysis of the sample image of the fluid canister can be further fed into analyses of sample images of surgical sponge gauzes, implements, surfaces, etc. to map total blood and/or other fluid loss of the patient over time. However, the first preferred method S100 can function in any other way to estimate the volume of blood within the physical sample that is a fluid canister.

One variation of the first preferred method S100 further comprises estimating the volume of extracorporeal non-blood fluids in the physical sample, such as ascites, saline irrigant, bile, plasma, urine, or saliva. In one example implementation, the redness of the physical sample (e.g., color intensity of image pixels associated with the physical sample in the red component space) is correlated with a total red blood cell count or volume in the physical sample, wherein the total red blood cell count or volume is subtracted from the estimated total extracorporeal blood volume in the sample, according to an estimated or measured hematocrit of the blood in the physical sample, to estimate the total volume of plasma in the physical sample. In another example implementation, the estimated total extracorporeal blood volume is converted to as estimated total extracorporeal blood weight (or mass), wherein the estimated total extracorporeal blood weight (or mass) and dry weight (or mass) of the physical sample are subtracted from a wet weight (or mass) of the physical sample to estimate the total weight (or mass of volume) of substantially clear fluids (e.g., saline, intestinal ascites) in the physical sample. In this example implementation, the first preferred method S100 preferably accessed a mass or weight measurement of the physical sample through a scale electrically coupled to the machine or device implementing the first preferred method S100. Furthermore, the first preferred method S100 preferably implements machine vision techniques to determine the type of physical sample, such as a surgical dressing, a surgical gauze sponge, or a surgical towel from a particular manufacturer. The first preferred method S100 can then access sample-specific data such as dry weight, absorptivity, fluid and/or saturation volume to enable extraction of further data related to blood or non-blood fluids in the physical sample. However, the first preferred method S100 can implement any other technique or method to estimate the volume, weight, or mass of an extracorporeal non-blood fluid in the physical sample.

However, the first preferred method can additionally or alternatively analyze one or more extracted and/or non-image features to estimate any one or more of hemoglobin mass, hematocrit, hemoglobin concentration, fresh frozen plasma, packed red blood cells, colloids, platelets, crystalloid, or any other blood-related parameter of the patient. Any one or more of these blood-related parameters can additionally or alternatively be rendered on a display of the machine, system, or device implementing the first preferred method S100.

One variation of the first preferred method includes recognizing gestures of a user to control operation of the machine, system, or device implementing the first preferred method S100. In this variation, the preferred method preferably accesses a live video feed captured by the optical sensor that records the image of the physical sample or by any other optical sensor or camera coupled to the machine, system, or device implementing the first preferred method S100. Because the first preferred method is preferably implemented during a surgery or other medical event or emergency during which a user is likely wearing a glove, the first preferred method S100 is preferably controlled via non-contact means. Generally, this variation of the first preferred method S100 preferably recognizes non-contact hand gestures. In one example, a 'thumbs up' can indicate that the user accepts the detection of the physical sample and the extracorporeal blood volume estimation of the physical sample. The extracorporeal blood volume can then be added to an aggregate extracorporeal blood volume estimated for a set of physical samples. Similarly, a 'thumbs down' can reject the detection and extracorporeal blood volume estimation for the physical sample. In another example implementation, a user can scroll through available physical sample types by sweeping a hand to the left or right. Similarly, the user can scroll through images of previous samples by sweeping a hand vertically. However, any other gesture can be recognized in any other way to control any other function of the first preferred method S100.

Another variation of the first preferred method S100 further functions to generate alarms or warnings related to the circulatory system of a patient. In one example, the preferred method S100 generates a warning that a physical sample that is a surgical sponge gauze was lost or left inside the patient if not identified within a threshold time (e.g., one hour) after being checked into a surgery. In another example, the first preferred method S100 sounds an alarm when the total estimated blood or red blood cell loss of the patient surpasses a threshold level. In this example, the threshold blood or red blood cell volume can be unique to the patient and based upon any one or more of the age, gender, weight, medical history, etc. of the patient. In another example, the first preferred method S100 issues a warning of trends in patient blood loss, such as based upon blood distribution across multiple physical samples (e.g., sponges) over time. However, the first preferred method can additionally or alternatively provide data and/or warnings relating to a rate of blood loss, a rate of blood loss relative to sponge count, a rate of sponge usage, a histogram of sponge usage, or any other suitable data or warning related to the circulatory system of the patient.

2. Second Method

As shown in FIG. 2, a second preferred method S200 for estimating the extracorporeal blood volume in a portion of a physical sample, includes: comparing a portion of an image of the sample with a template image of known extracorporeal blood volume indicator in Block S210; tagging the portion of the image of the sample with a blood volume indicator according to the template image that is matched to the portion of the image of the sample in Block S220; and estimating the extracorporeal blood volume in at least a portion of the physical sample, associated with the portion of the image of the sample, according to the blood volume indicator in Block S230.

The second preferred method S200 preferably implements non-parametric estimation (e.g., template matching) of extracorporeal blood volume in the physical sample, as described above. Generally, Block S220 preferably incorporates a variation of Block S220 of the first preferred method S100, and Block S230 preferably incorporates a variation of Block S130 of the first preferred method S100. However, as shown in FIG. 3B, the second preferred method S200 can implement any other technique, method, implementation, and/or variation of the first preferred method S100 described above.

One variation of the second preferred method S200 includes accessing the template image that is a color model paired with a blood volume indicator. The color model can be a template image, a representation of or feature extracted from a template image, a mathematical function or algorithm, or any other suitable color model correlating an extracted feature of the sample image with a blood volume indicator. In this variation, Block S210 can include comparing the portion of the image of the sample with the template image to generate the blood volume indicator tag that is a composite of the known blood volume indicators of the multiple color models, such as a first and a second template image that each include a color model paired with a blood volume indicator.

Block S220 of the second preferred method S200 can include tagging the portion of the image of the sample with the blood volume indicator that is an estimated hemoglobin mass. Furthermore, Block S230 of the second preferred method S200 can include estimating the extracorporeal blood volume in at least the portion of the physical sample according to the hemoglobin mass and an estimated hematocrit of blood in the physical sample. However, Blocks S220 and S230 of the second preferred method S200 can function in any other way, and the second preferred method can implement any other Block, variation, example, or implementation of the first preferred method S100.

3. Third Method

Figure 3A:
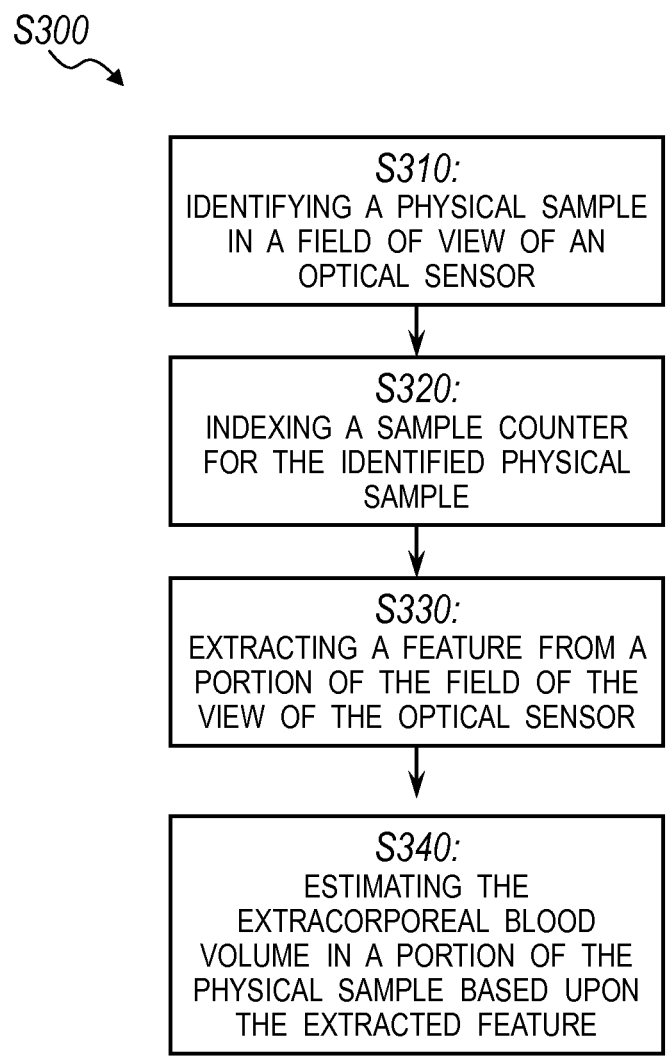
FIG. 3A is a flowchart representation of a method of a third preferred embodiment.
Figure 3B:
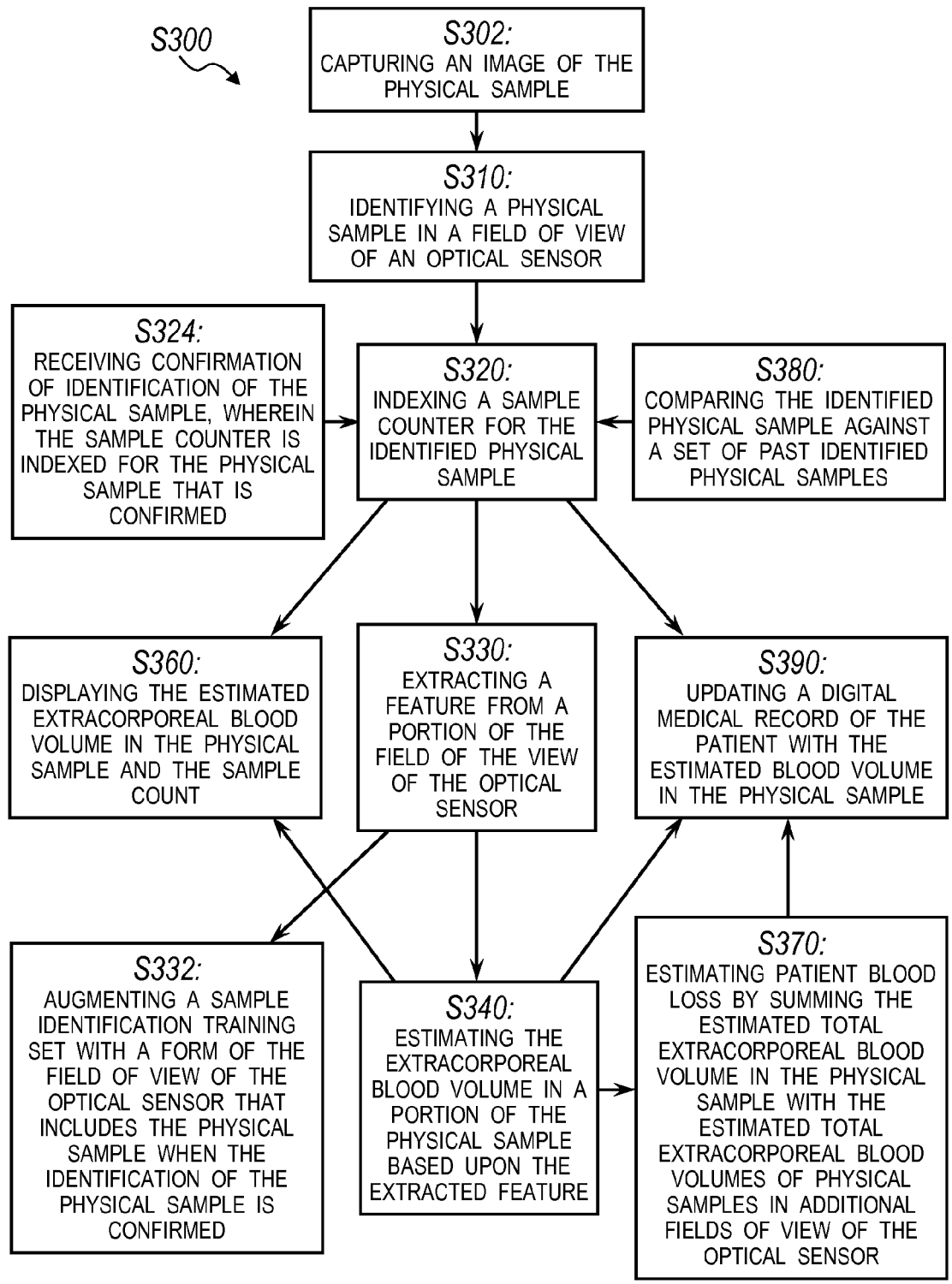
FIG. 3B is a flowchart representation of one variation of the third preferred method.

As shown in FIG. 3A, a third preferred method S300 for counting physical surgical samples includes: identifying a physical sample in a field of view of an optical sensor in Block S310; indexing a sample counter for the identified physical sample in Block S320; extracting a feature from a portion of the field of the view of the optical sensor in Block S320; and estimating the extracorporeal blood volume in a portion of the physical sample based upon the extracted feature in Block S340.

The third preferred method S300 preferably functions to identify a physical sample, update a sample count, and estimate the volume of blood in the physical sample by analyzing the field of view of the optical sensor that includes the physical sample. The field of view of the optical sensor is preferably captured in the form of a static or still image of the sample. The physical sample is preferably identified in the field of view of an optical sensor in Block S310, which preferably triggers Block S302 to capture the image of the physical sample, wherein the image of the physical sample is only taken once the physical sample is identified. Alternatively, the image of the sponge can be captured in Block S302 and subsequently analyzed in Block S310 to identify the physical sample visible therein.

The physical sample can be any of a surgical dressing, a surgical gauze sponge, a surgical towel, or any other absorbent textile used to collect blood or other bodily fluids. Like the first preferred method S100, a surgeon, nurse, anesthesiologist, gynecologist, soldier, paramedic, or other user can preferably use a machine, system, or device implementing the third preferred method S300 to maintain a count of and to estimate extracorporeal blood volume in surgical towels, gauze sponges, or other absorbent textiles. By summing the estimated blood volumes across multiple towels or gauze sponges, an estimated blood loss (EBL) for a patient can be estimated. The third preferred method S300 can therefore be useful in a hospital setting, such as in a surgical operating room, or in a clinical setting, such as in a delivery room, or in any other suitable setting.

Like the first preferred method S100, the third preferred method S300 is preferably implemented in a handheld or mobile electronic device, such as a native application or 'app' executing on a digital music player, a PDA, a smartphone, or a tablet computer. For example, a camera or other optical sensor integral with the electronic device can capture the image of the sample in Block S302, a processor integral with the electronic device can perform Blocks S310, S320, and S330, and S340, and a display integral with the electronic device can display the sample count and the estimated blood volume in the physical sample and/or across multiple physical samples in Block S360. In this variation, the electronic device can also communicate with a remote server that performs at least some of Blocks S310, S320, S330, and S340. However, the third preferred method S300 can be implemented in any other system, device, or combination thereof.

As shown in FIG. 3A, Block S310 of the third preferred method S300 recites identifying the physical sample in the field of view of the optical sensor. The field of view of the optical sensor can be a static image or a video that was taken previously, wherein Block S310 identifies the physical sample in the static image or video substantially after the image or video was taken. However, the field of view of the optical sensor is can alternatively be a live feed from the optical sensor, wherein Block S310 identifies the physical sample in the field of view substantially in real time. The image is preferably a color image captured by any of a digital color camera, an RGB camera, or any number of charge-coupled device (CCD) sensors, complimentary metal-oxide-semiconductor (CMOS) active pixel sensors, or other optical sensors of any other type. Furthermore, the optical sensor can capture the image of the sample in any other form or across any other wavelength or range of wavelengths in the visible spectrum, infrared spectrum, or any other spectrum.

Block S310 preferably implements machine vision to identify content in the field of view as including or not including a suitable sample that is surgical sponge gauze, towel, or dressing. In one variation of the third preferred method S300, Block S310 uses edge detection to estimate the perimeter of the physical sample visible in the field of view and then determines a physical dimension of the physical sample, such as length and width in inches, through gauging. The dimension of the physical sample can be estimated by transforming the field of view according to a known or anticipated distance or angle between the optical sensor and the physical sample, by estimating distance and angle according to shadows or objects of known dimension in the field of view, by accessing data from an infrared, laser, sonic, or other range finder arranged proximal the optical sensor, or by any other suitable technique or device. By comparing the physical dimension(s) of the physical sample to template samples in a library of suitable samples of known dimension(s), Block S310 can determine both the presence, size, and/or and type of a physical sample in the field of view of the optical sensor.

In another variation of the third preferred method S300, Block S310 also implements edge detection to determine a boundary of the physical sample visible in the field of view and subsequently removes substantially all of the field of view that is outside the estimated boundary of the physical sample. Block S310 then performs image matching to compare generally the boundary of the physical sample visible in the field of view with boundaries of template samples in a library of proper physical samples. In this variation, deviation in boundary path, color property, contrast with a background, or other property of the estimated physical sample relative the template sample beyond a specified threshold can indicate that the sample in the field of view is not a suitable sample.

In a further variation of the third preferred method S300, Block S310 implements pattern recognition and machine learning to determine the presence and/or type of physical sample in the field of view of the optical sensor. This variation preferably incorporates supervised machine learning, wherein Block S310 accesses a set of training data that includes template images properly labeled as including or not including a suitable sample. A learning procedure then preferably transforms the training data into generalized patterns to create a model that can subsequently be used to analyze the field of view of the optical sensor an detect a proper physical sample shown therein. However, Block S310 can alternatively implement unsupervised learning or semi-supervised learning (e.g. clustering, mixture of Gaussians, GrabCut) in which at least some of the training data has not been labeled. In this variation, Block S310 can further implement feature extraction, feature dimensionality reduction (e.g., principle component analysis (PCA)), feature selection, or any other suitable technique to prune redundant or irrelevant features from the field of view of the optical sensor (or the image).

In any of the foregoing variations of the third preferred method S300, the third preferred method S300 preferably accepts an input indicative of an improper identification of a physical sample in the field of view. The input, preferably provided by a surgeon, nurse, anesthesiologist, gynecologist, or other user, can indicate that the field of view does include a suitable sample when Block S310 incorrectly determines that the field of view does not include a suitable sample. Also or alternatively, the input can indicate that the field of view does not include a suitable sample when Block S310 incorrectly determines that the field of view does include a suitable sample. This input is then preferably fed back into the set of training data, wherein the input is assumed correct, the field of view is labeled with the input, and the field of view (or image) and input tag are added to the training set, such as in Block 332 shown in FIG. 3B. In the event that the determination of Block S310 is not corrected via such an input, the field of view can also be fed back into the set of training data, wherein the determination of Block S310 is assumed correct absent corrective input, the field of view is labeled with the determination of Block S310, and the field of view (or image) and determination tag are added to the training set. Through this form of closed feedback, the training set can grow perpetually and continue to teach Block S310, which may substantially improve the machine-learning algorithm and improve the accuracy of Block S310.

Block S310 can therefore implement any of segmentation, localization, edge detection, gauging, clustering, pattern recognition, template matching, feature extraction, principle component analysis (PCA), feature dimensionality reduction, feature selection, thresholding, positioning, color analysis, closed feedback, or any other type of machine learning or machine vision. Such methods preferably compensate for varying lighting conditions of the physical sponge, warping of the physical sample (e.g., a wrinkle or warped sponge), warping of the image of the physical sample (e.g., due to optical distortion caused by the optical sensor), or any other inconsistency or variable common in use scenarios Block S310 can additionally or alternatively function to identify other relevant objects, materials, or fluids in the field of view of the optical sensor. For example, the aforementioned machine vision techniques can again be similarly implemented in Block S310 to identify blood droplets, drops, pools, or smears on a surgical tool, tray, table, wall, floor, or other surface. Such bloodies articles can also or alternatively be added to the sample count in Block S320 and/or analyzed in Blocks S330 and/or S340.

However, Block S310 can further include identifying additional physical samples in fields of view of the optical sensor and indexing the sample counter for the identified additional physical samples, either in series before or after identifying the physical sample or substantially simultaneously while identifying the physical sample. In this variation, Block S310 can implement and one or more of the same or different aforementioned methods or techniques to identify the additional physical samples in the field of view of the image.

As shown in FIG. 3B, one variation of the third preferred method S300 includes Block S302, which recites capturing the image of the physical sample. As described above, Block S302 can trigger Block 110, wherein Block S302 captures the image and Block S310 subsequently identifies the presence of a suitable sample in the field of view that is the image. In this variation, an input from a surgeon, a nurse, an anesthesiologist, a gynecologist, or any other user can trigger Block S302. However, Block S310 preferably triggers Block S302 when a suitable sample is identified in the field of view of the optical sensor. In this variation, a user preferably places the physical sample within the field of view of the optical sensor, Block S310 identifies the physical sample, and Block S302 captures the image of the sample automatically. The physical sample is preferably held at a substantially known angle between and/or distance from the optical sensor such that a dimension of the physical sample in the field of view can be estimated, such as through gauging described above.

The image of the physical sample captured in Block S302 is preferably a color image of the physical sample against a background, wherein the image is subsequently presented to a user on a digital display in Block S360 with the sample count and the estimated blood volume in the sample defining an augmented reality overlay. Alternatively, the image can be: a color image of the physical sample with the background removed; an infrared image or black and white image; a fingerprint of the field of view, such as with pointers or indicators of unique identifying features of the physical sample; or any other suitable type of image. The image is preferably stored for later access, such as in the variation of the third preferred method S300 that includes Block S380 in which the identified physical sample is checked for a duplicate physical sample identified in a previous field of view or image. The image can be stored locally, such as on a data storage module arranged within a handheld electronic device performing at least some Blocks of the third preferred method S300, or remotely, such as in digital memory accessed through a remote server or a local network.

As shown in FIG. 3A, Block S320 of the third preferred method S300 includes indexing the sample counter for the identified physical sample identified. The sample counter is preferably a cumulative counter of successive physical samples identified as a surgical dressing, a surgical gauze sponge, or a surgical towel. In Block S320, physical samples of various types can be tallied together in one group, though physical samples of various types can alternatively be tallied in separate groups. In this alternative, the groups can be defined according to genus, such as according to sample type including a surgical dressing group, a surgical gauze sponge group, or a surgical towel group. In this alternatively, the groups can also be defined according to species, such as according to manufacture or purpose including a Ray-Tec surgical gauze group and a laparotomy surgical gauze group. Furthermore, the sample count can include a tally of other blood-related samples, such as blood drops, pools, or smears of certain sizes or estimated blood volumes, though the sample count can track the number of any other relevant physical sample of any other type.

As shown in FIG. 3B, one variation of the preferred method includes Block S324, which recites receiving confirmation of identification of the physical sample. In this variation, Block S320 preferably indexes the sample counter only for the physical sample that is confirmed. Sample confirmation is preferably provided by a user, such as through a touch-free gesture recognition or via a foot pedal, as described below.

The sample count is preferably displayed to a user, such as through a display in Block S360. The sample count is also preferably updated and stored on a local or remote hard drive or data storage device accessible by the machine or system performing at least portions of the third preferred method S300.

Block S330 of the third preferred method S300 recites extracting a feature from a portion of the field of the view of the optical sensor. Block S340 of the third preferred method S300 recites estimating the extracorporeal blood volume in a portion of the physical sample based upon the extracted feature. Therefore, Blocks S330 and S340 of the third preferred method S300 preferably cooperate to estimate extracorporeal blood volume in the physical sample according to any one or more methods of the first preferred method described above.

In one variation of the third preferred method S300, the field of view of the optical segment or the image (the 'image segment') is statically segmented according to predefined segment size and/or shape, such as a square ten-pixel by ten-pixel area. Alternatively, image segment can be dynamically segmented, such as according to redness, hue, saturation, shade, brightness, chroma, wavelength range, or any other metric of color or light in the field of view or in the image. Each segment of the image segment is preferably decomposed into separate color components (e.g., red, green, and blue), and for each color component, the absolute difference in pixel intensity for the pixels in the image segment and a template image is calculated. The image segment is preferably thus compared against available template images until a suitable match is found. Each template image in the library of template images is preferably an image of a master sample of known extracorporeal blood volume, hematocrit, red blood cell or hemoglobin volume, density, and/or any other suitable blood-related parameter or blood volume indicator. Specifically, each template image preferably includes information to inform the blood volume or blood volume indicator of the image segment. Furthermore, in Block S340, the blood volume indicator can be converted into a blood volume, a hemoglobin or red blood cell mass or volume, or other blood-related metric, such as correlated with an estimated physical dimension of a portion of the physical sample identified in the image segment. Once each segment of the image or field of view is tagged with a blood volume or indicator, the blood volume or indicator tags of all image segments of the identified physical sample visible in the image can be summed to estimate the total blood volume or indicator in the physical sample.

The library of template images can additionally or alternatively be a color palette, wherein each template image is a different color indicative of a different blood volume or blood volume indicator, such as rather than each template image being of a physical master sample of known blood volume or indicator. In this alternative, the library is preferably a color palette for different types of absorbent surgical sponge gauzes, dressings, and towels, wherein each color (i.e. template image) in a color palette for a particular type of physical sample is associated with a particular blood volume or blood volume indicator. In this variation, the template image that is a color can be an image of the color or a numerical color identifier, such as a HEX code value (e.g., #FF0000, #A00000, #880000, etc.) or an RGB code value (e.g., (255, 0, 0), (160, 0, 0), (190, 0, 0), etc.).

In this variation of the third preferred method S300, processing time required to find a template image match for each image segment can be reduced by avoiding comparison of each image segment with certain template images substantially dissimilar from the image segment. Template images of master samples of surfaces, products, materials, or dimensions substantially dissimilar from that of the physical sample can be excluded from comparison. Thresholding can also be used to remove substantially irrelevant template images from the test pool. For example, template images with redness values (e.g., intensity, hue, saturation, shade, brightness, chroma, wavelength range) or physical dimensions substantially dissimilar from that of the image segment can be excluded from comparison. Tree searching can also be used to reduce processing time. However, template images can be grouped in the template library and selected or deselected from comparison with the image segment in any other way.

In another variation of the third preferred method S300, the image library is substantially large enough that the entire portion of the image or field of associated with a proper physical sample is compared against template images in the library, and the blood volume or blood volume indicator is directly estimated for the entire physical sample without segmentation.

In a further variation of the third preferred method S300, a redness value is calculated for each image segment. Redness value can be intensity of a wavelength or composite intensity of a range of wavelengths of light, redness hue, redness saturation, RGB code value (e.g., (0, 0, 0) through (255, 0, 0)) or any other suitable metric over the image segment. Preferably, the image of the sample is decomposed into distinct color spaces (e.g., red, green, and blue), wherein a redness value is calculated for the image segment in at least the red color space. The redness value of the image segment can then be converted into a blood volume or blood volume indicator, such as through a lookup table, a regression model, a non-negative least-squares algorithm, or any other suitable algorithm, model, or method. For example, reflectance of oxygenated hemoglobin (HbO2) can be correlated with certain wavelengths of light to substantially directly estimate the volume or mass of hemoglobin in the portion of the physical sample identified in the image segment.

In still another variation of the third preferred method S300, the image or field of view is not segmented, and a redness value is instead calculated for the entire portion of the image or field of view correlated with the physical sample. The redness value can be an average or weighted average of redness, hue, saturation, shade, brightness, chroma, wavelength range, or any other metric of color or light of the identified image sample. As in a variation above, the blood volume or blood volume indicator for the entire portion of the physical sample identified in the field of view or in the image can be estimated according to the redness value.

As shown in FIG. 3B, one variation of the third preferred method S300 further includes Block S360, which recites displaying the estimated extracorporeal blood volume in the physical sample and the sample count. This data is preferably presented on a digital display of a machine or system configured to perform the Blocks of the third preferred method S300. This data can be presented in the form of an augmented reality overlay on top of the static sample image depicted on the display, in the form of a dynamic augmented reality overlay on top of a live video stream captured by the optical sensor and depicted on the display, in the form of a table, chart, or diagram including the sample count and the singular and/or cumulative estimated blood volumes in one or more physical samples over a period of time or during a medical event or emergency, or in any other suitable form. This may be useful in estimating patient risk, in determining when to administer saline or to provide a blood transfusion, in maintaining record of surgical events, and/or in estimating future blood-related events or patient needs. Other blood-related metrics can also be estimated in the third preferred method S300 and presented in Block S360, such as blood spread rate, blood surface area, patient risk level, extracorporeal non-blood fluid volume, or patient hemorrhage classification. However, the sample count, estimated blood volume(s), and/or any other blood-related metric or patient information can be presented in any other way or form in Block S360.

As shown in FIG. 3B, another variation of the third preferred method S300 includes Block S380, which recites comparing the identified physical sample against a set of past identified physical samples. In this variation, the sample counter is preferably indexed in Block S120 only when the identified physical sample is determined to be unique amongst the set of past identified physical samples. The image of the sample, a fingerprint of the sample image, the extracted feature of the image, or other identifying feature of the physical sample in the image can be compared with images, fingerprints, extracted features, and/or other identifying features of images of previous physical samples. Block S380 preferably substantially therefore preferably prevents double counting of the physical sample in the sample count of Block S320 and/or prevents double counting of the estimated volume of blood in a total extracorporeal blood volume estimate across multiple physical samples or total estimated blood loss of a patient. In Block S380, comparison of the sample image with a previous sample image can require image fingerprinting or a scale, rotation, mirror, stretch or other transformation of either the sample image or the previous sample image. Edge detection, pattern recognition, and/or other machine vision techniques can additionally or alternatively be used to determine the uniqueness of bloodied regions of the physical sample visible in the sample image, relative to bloodied regions of a previous physical sample. However, Block S380 can function in any other way to identify the physical sample as shown in a previous sample image.

As shown in FIG. 3B, another variation of the third preferred method S300 includes Block S390, which recites updating a digital medical record of the patient with the estimated blood volume in the physical sample. Block S190 can additionally or alternatively update the medical record of the patient with the estimated blood volume across multiple physical samples, the estimated blood loss of the patient, patient blood loss trends, or any other relevant metric or data generated related to the circulatory system of a patient. The digital medical record can be maintained locally on a machine or system implementing the third preferred method S300 or on a local network or remote server accessed by the machine or system to retrieve, update, and/or upload the digital medical record.

The third preferred method S300 can further implement any one or more methods, Blocks, or variations of the first preferred method S100.

4. Systems

Figure 8:
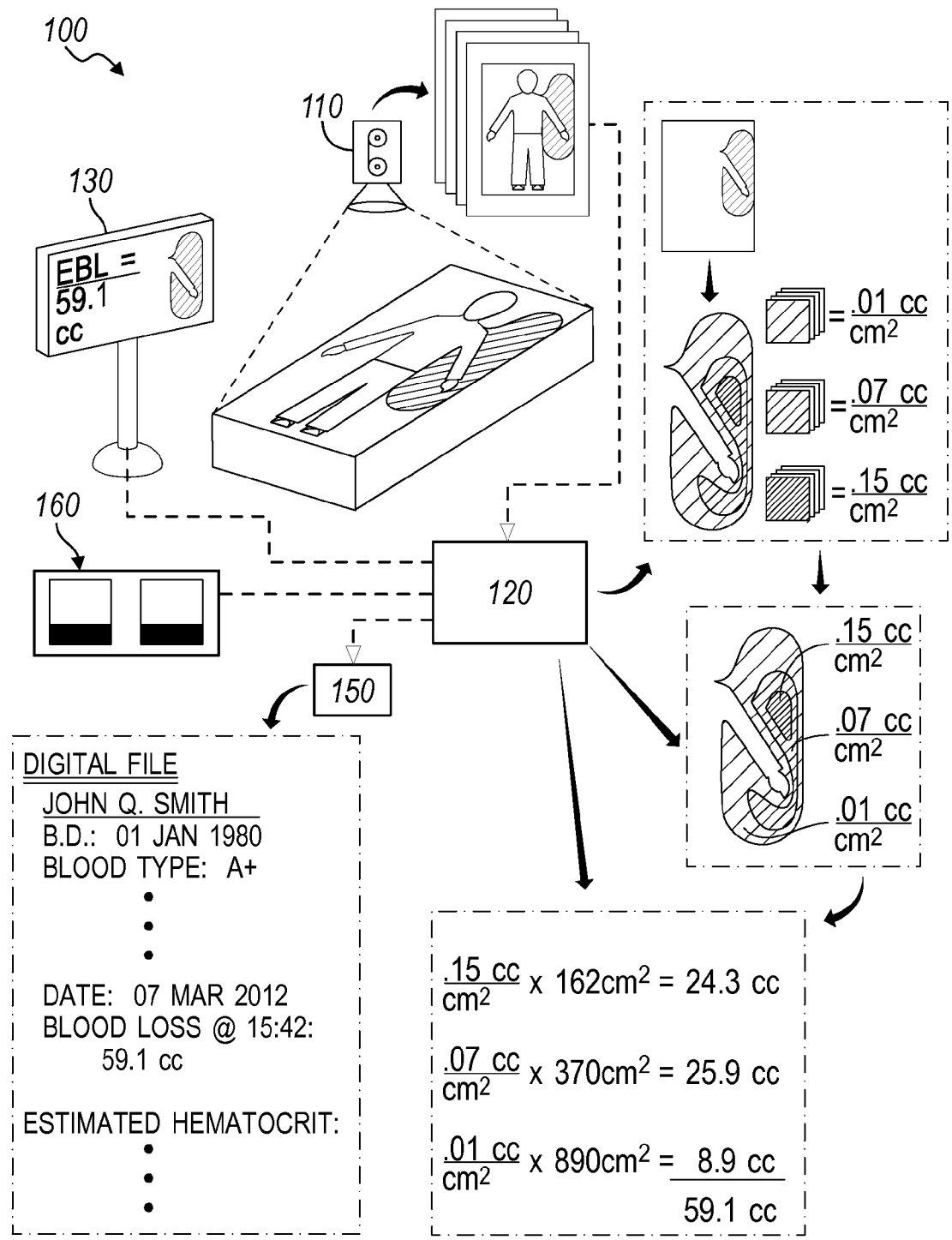
FIG. 8 is a schematic of a system of a preferred embodiment.

As shown in FIGS. 8 and 9, a preferred system 100 for estimating the extracorporeal blood volume in a portion of a physical sample includes: an optical sensor 110, a processor 120, and a display 130. The optical sensor 110 captures an image of the physical sample (the 'sample image'). The processor 120 extracts a feature from a portion of an image of the sample, tags the portion of the image of the sample with a blood volume indicator according to the extracted feature, and estimates the extracorporeal blood volume in at least a portion of the physical sample, identified in the portion of the image of the sample, according to the blood volume indicator. The display 130 depicts the estimated blood volume in at least the portion of the physical sample.

The system 100 preferably functions to estimate the volume of blood in the sample by analyzing the sample image. The preferred system 100 is configured and/or adapted to perform one or more Blocks of the first preferred method S100. As described above, the sample is preferably an absorbent surgical gauze sponge, though the sample can also be a table or floor surface, a piece of clothing, an external skin surface or surgical glove, a surgical implement, a fluid canister, or any other surface or material. A surgeon, nurse, anesthesiologist, gynecologist, doctor, soldier, or other user can preferably use the system 100 to estimate blood volume in one sample and then sum the estimated blood volume in the sample with estimated blood volumes in other samples to generate a total estimated blood loss (EBL) of a patient during a surgery, child birth, or other medical event or situation.

The preferred system 100 can alternatively function to estimate the content (e.g., volume, mass) of another blood-related parameter or extracorporeal blood volume indicator in the sample, such as hemoglobin, (HGB) or red blood cell (RBC) content of the sample. Furthermore, the preferred system 100 can additionally or alternatively function to detect presence of blood in the sample, compute blood spread rate, calculate blood surface area, estimate patient risk level (e.g., hypovolemic shock), and/or determine hemorrhage classification of the patient. However, the preferred system 100 can provide any other functionality, analyze any other image type or format, estimate any other blood-related parameter, and calculate blood volume in the physical sample in any other way.

As shown in FIG. 9, the preferred system 100 can be configured as a handheld (e.g., mobile) electronic device, such as a smartphone or tablet running an image-based blood estimation application (or app) and including the camera 110, the processor 120, and the display 130. Alternatively, the components of the preferred system 100 can be substantially discreet and distinct (i.e., not contained within a single housing). For example and as shown in FIG. 7, the optical sensor no can be a camera substantially permanently arranged within an operating room, wherein the camera communicates with a local network or a remote server (including the processor 120) on which the sample image is analyzed (e.g., according to the method S100), and wherein a display 130 that is a computer monitor, a television, or a handheld (mobile) electronic device accesses and displays the output of the processor 120. However, the preferred system 100 can be of any other form or include any other component.

The preferred system 100 can preferably be used in a variety of settings, including in a hospital setting, such as in a surgical operating room, in a clinical setting, such as in a delivery room, in a military setting, such as on a battlefield, or in a residential setting, such as aiding a consumer in monitoring blood loss due to menorrhagia (heavy menstrual bleeding) or epistaxis (nosebleeds). However, the preferred system 100 can be used in any other setting.

The optical sensor no of the preferred system 100 functions to capture the image of the physical sample. The optical sensor no preferably implements Block S102 of the preferred embodiment. The optical sensor 110 is preferably a digital camera that captures a color sample image or an RGB camera that captures independent image components in the red, green, and blue fields. However, the optical sensor no can comprise any number of cameras, charge-coupled device (CCD) sensors, complimentary metal-oxide-semiconductor (CMOS) active pixel sensors, or optical sensors of any other type. Furthermore, the optical sensor 110 can capture the sample image in any other form or across any other wavelength or range of wavelengths in the visible spectrum, infrared spectrum, or any other spectrum.

The optical sensor 110 is preferably a camera arranged within a handheld electronic device, as shown in FIG. 8. However, the optical sensor no can also or alternatively be a camera or other sensor configured to be mounted on a pedestal for placement in an operating room, configured to be mounted to a ceiling over an operating table, configured for attachment to a battlefield helmet of a field nurse, configured to mount to a standalone blood volume estimation system including the processor 120, the display 130, and a staging tray that supports the physical sample for imaging, or configured for placement in or attachment to any other object or structure.

The processor 120 of the preferred system extracts a feature from a portion of an image of the sample, tags the portion of the image of the sample with a blood volume indicator according to the extracted feature, and estimates the extracorporeal blood volume in at least a portion of the physical sample, identified in the portion of the image of the sample, according to the blood volume indicator. The processor 120 can preferably perform the Blocks of the first preferred method S100 described above.

The processor 120 can be coupled to the optical sensor 110, such as via a wired connection (e.g., a trace on a shared PCB) or a wireless connection (e.g., a Wi-Fi or Bluetooth connection), such that the processor 120 can access the sample image captured by or visible in the field of view of the optical sensor no. In one variation, the processor 120 is arranged within a handheld electronic device that also contains the optical sensor no and the display 130. In another variation, the processor 120 is a portion of or is tied to a remote server, wherein image data from the optical sensor 110 is transmitted (e.g., via an Internet or local network connection) to the remote processor 120, wherein the processor 120 estimates the extracorporeal blood volume in at least the portion of the physical sample by analyzing the sample image, and wherein the blood volume estimate is transmitted to the display 130.

In one variation of the preferred system 100 and as described above, the processor 120 can pair the portion of the sample image to the template image via template matching, and the template image is preferably one template image in a library of template images. In another variation of the preferred system 100 and as described above, the processor 120 parametrically generate the blood volume indicator based upon at least one extract feature from the image of the sample. The processor 120 can therefore be in communication with a local or remote data storage module, such as a hard drive in the handheld electronic device or a memory module of a remote server. The processor 120 can further upload the sample image for checking subsequent sample images against duplicate analysis of the same physical sample, for example as described with reference to Block 180 of the first preferred method S100. Finally, the processor 120 can analyze different types of images (e.g., static, streaming, .MPEG, .JPG, .TIFF) and/or images from one or more distinct cameras or optical sensors.

The display 130 of the preferred system 100 preferably depicts the estimated blood volume in at least the portion of the physical sample. The display 130 is preferably arranged within the handheld electronic device (e.g., smartphone, tablet, personal data assistant) that also contains the optical sensor 110 and the processor 120, as shown in FIG. 8. Alternatively, the display can be a computer monitor, a television screen, or any other suitable display physically coextensive with any other device, as shown in FIG. 7. The display 130 can therefore be any of an LED, OLED, plasma, dot matrix, segment, e-ink, or retina display, a series of idiot lights corresponding to estimated blood volume, or any other suitable type of display. Finally, the display 130 can be in communication with the processor 120 via any of a wired and a wireless connection.

The display 130 can preferably perform at least Block S160 by depicting the estimated blood volume in the portion of the physical sample, in the whole of the physical sample, and/or across multiple physical samples. The blood volume estimate is preferably depicted in a common form, such as "cc's" (cubic centimeters). As shown in FIG. 8, this data can be presented in the form of a dynamic augmented reality overlay on top of a live video stream of the physical sample that is also depicted on the display 130, wherein images from the optical sensor 110 are relayed substantially in real time, through the processor 120, to the display 130. As shown in FIG. 8, the data can alternatively be presented in a table, chart, or graph depicting at least one of a time-elapse cumulative estimated blood volume across multiple samples analyzed over time and individual blood volume estimates for each physical sample. The display 130 can also depict: previous sample images; warnings, such as patient risk level (e.g., hypovolemic shock), or a hemorrhage classification of the patient; or suggestions, such as begin blood transfusion. Any of these data, warnings, and/or suggestions can also be depicted across multiple screens or made available for access on any one of more displays.

As shown in FIG. 9, one variation of the preferred system 100 can further include a handheld housing 140 configured to contain the optical sensor 110, the processor 120, and the display 130. The handheld housing 140 with optical sensor no, processor 120, and display 130 can define a handheld (mobile) electronic device capable of estimating blood volume in one or more physical samples in any number of suitable environments, such as in an operating room, a delivery room, a battlefield, a crime scene, and a home.

In another variation of the preferred system 100 shown in FIG. 8, the housing 140 further contains a wireless communication module 150 that communicates the estimated blood volume in the portion of the physical sample to a remote server configured to store an electronic medical record of a patient. The medical record is also preferably updated with estimated blood loss over time, patient risk level, hemorrhage classification, and/or other blood-related metrics or blood volume indicators. The patient medical record can therefore be updated substantially automatically during a medical event, such as a surgery or childbirth. The housing 140 is preferably of a medical-grade material such that the system 100 that is a handheld electronic device is suitable for use in an operating room or other medical or clinical setting. The housing can therefore be medical-grade stainless steel, such as 316L stainless steel, a medical-grade polymer, such as high-density polyethylene (HDPE), or a medical-grade silicone rubber. However, the housing can be of any other material or combination of materials.

As shown in FIG. 9, a variation of the preferred system 100 further includes a foot pedal 160 accessible by a user to confirm or to refute the identity of the physical sample. In this variation, the processor 120 preferably indexes the sample count when the user confirms the identity of the physical sample through the foot pedal 160. Additionally or alternatively, the user can engage the foot pedal 160 to select an appropriate sample type (e.g., a surgical sponge gauze, a surgical towel, a surgical dressing), to scroll through previous sample images, or to control the preferred system 100 in any other way. The foot pedal 160 therefore preferably includes at least two input regions that can be engaged by a foot of a user to manipulate the preferred system 100.

In one variation of the preferred system 100, the processor additionally or alternatively compares a portion of the image of the sample with a template image of known blood volume indicator, tags the portion of the image of the sample with a blood volume indicator according to the template image that is matched to the portion of the image of the sample, and estimates the extracorporeal blood volume in at least a portion of the physical sample, associated with the portion of the image of the sample, according to the blood volume indicator.

In a further variation of the preferred system 100, the processor additionally or alternatively identifies the physical sample in the image, indexes a sample counter for the identified physical sample, extracts a feature from a portion of the image, estimates the extracorporeal blood volume in a portion of the physical sample based upon the extracted feature. The preferred system 100 can therefore implement the first preferred method, the third preferred method, and/or any combination or variation thereof.

The systems and methods of the preferred embodiments can be embodied and/or implemented at least in part as a machine configured to receive a computer-readable medium storing computer-readable instructions. The instructions are preferably executed by computer-executable components preferably integrated with the system, the optical sensor, the processor, the display, hardware/firmware/software elements of a system or handheld electronic device, or any suitable combination thereof. Other systems and methods of the preferred embodiments can be embodied and/or implemented at least in part as a machine configured to receive a computer-readable medium storing computer-readable instructions. The instructions are preferably executed by computer-executable components preferably integrated by computer-executable components preferably integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component is preferably a processor but any suitable dedicated hardware device can (alternatively or additionally) execute the instructions.

As a person skilled in the art of estimating the extracorporeal blood volume in a physical sample will recognize from the previous detailed description and from the figures and claims, modifications and changes can be made to the preferred embodiments of the invention without departing from the scope of this invention defined in the following claims.

We claim:

1. A method for estimating the extracorporeal blood volume in a portion of a physical sample, the method comprising:
    extracting a feature from a portion of an image of the sample;
    tagging the portion of the image of the sample with a blood volume indicator according to the extracted feature; and
    estimating the extracorporeal blood volume in at least the portion of the physical sample associated with the portion of the image of the sample, according to the blood volume indicator;
    wherein extracting the feature from the portion of the image of the sample comprises extracting the feature that comprises a color intensity value in a component space; and
    wherein tagging the portion of the image of the sample with the blood volume indicator comprises transforming the extracted feature into the blood volume indicator according to a parametric model.

2. A method for estimating the extracorporeal blood volume in a portion of a physical sample, the method comprising:
    extracting a feature from a portion of an image of the sample;
    tagging the portion of the image of the sample with a blood volume indicator according to the extracted feature; and
    estimating the extracorporeal blood volume in at least the portion of the physical sample associated with the portion of the image of the sample, according to the blood volume indicator;
    wherein estimating the extracorporeal blood volume in at least a portion of the physical sample comprises associating a physical dimension of the physical sample with the portion of the image of the sample by transforming the portion of the image according to at least one of an estimated distance and an estimated angle between the capture origin of the image and the physical sample.

3. The method of claim 2, wherein extracting the feature from the portion of the image of the sample comprises extracting a feature selected from the group consisting of a redness value in the red component space, a blueness value in the blue component space, a greenness value in the green component space, a surface area of the physical sample, a surface area of a bloodied region of the physical sample, a pixel count of the portion of the image associated with the portion of the physical sample, and a color intensity value of the portion of the image associated with an unsoiled portion of the sample.

4. A method for estimating the extracorporeal blood volume in a portion of a physical sample, the method comprising:
    extracting a feature from a portion of an image of the sample;
    tagging the portion of the image of the sample with a blood volume indicator according to the extracted feature; and
    estimating the extracorporeal blood volume in at least the portion of the physical sample associated with the portion of the image of the sample, according to the blood volume indicator;
    wherein tagging the portion of the image with the blood volume indicator comprises classifying the physical sample according to a non-image feature, selecting a blood volume indicator model based upon the classification of the sample, and generating the blood volume indicator tag by passing the extracted feature into the selected blood volume indicator model.

5. The method of claim 4, wherein the non-image feature is selected from the group consisting of current patient intravascular hematocrit, estimated patient intravascular hematocrit, historic patient intravascular hematocrit, weight of the sample, clinician-estimated sample blood volume, an ambient lighting condition, type of the sample, properties of the sample, a patient vital sign, patient medical history, an identity of a surgeon, and a type of surgery.

6. The method of claim 1, wherein estimating the extracorporeal blood volume in at least the portion of the sample comprises estimating the total extracorporeal blood volume in the physical sample based upon aggregated blood volume indicator tags of the portion of the image of the sample and substantially all other portions of the image.

7. The method of claim 6, further comprising estimating patient blood loss by aggregating the estimated total extracorporeal blood volume in the physical sample and estimated total extracorporeal blood volumes in additional physical samples in additional images.

8. The method of claim 6, further comprising estimating a volume of non-blood fluid in the physical sample by subtracting the weight of the estimated total extracorporeal blood volume in the physical sample from an entered weight of the physical sample.

9. The method of claim 2, further comprising capturing the image through an optical sensor incorporated into a mobile electronic device.

10. The method of claim 9, further comprising displaying, on a display incorporated into the mobile electronic device, the estimated extracorporeal blood volume in at least the portion of the physical sample.

11. The method of claim 2, further comprising updating a digital medical record of a patient with the estimated blood volume in at least the portion of the physical sample.

12. A system for determining the extracorporeal blood volume in a physical sample, the system comprising:
an optical sensor that captures an image of the physical sample;
a processor that extracts a feature from a portion of an image of the sample, tags the portion of the image of the sample with a blood volume indicator according to the extracted feature, and estimates the extracorporeal blood volume in at least a portion of the physical sample, identified in the portion of the image of the sample, according to the blood volume indicator; and
a display that depicts the estimated blood volume in at least the portion of the physical sample.

13. The system of claim 12, wherein the optical sensor is a camera, and wherein the processor further determines at least one of the angle of the camera relative to the physical sample and the distance between the camera and the physical sample at the time of the image was captured.

14. The system of claim 12, wherein the optical sensor is configured to be mounted overhead a surgical operating table.

15. The system of claim 12, further comprising a handheld housing that contains the optical sensor, the processor, and the display.

16. The system of claim 12, further comprising a wireless communication module that communicates the estimated blood volume in the portion of the physical sample to a remote server that stores an electronic medical record of a patient.

17. The system of claim 12, further comprising a data storage module configured to store a library of template images of known blood volume indicators, wherein the processor is configured to access a template image from the data storage module and to compare the template image with the portion of the image of the sample according to the extracted feature to generate the blood volume indicator tag.

18. The method of claim 2, further comprising identifying the physical sample in the image as a type of absorbent gauze sponge.

19. The method of claim 18, further comprising indexing a sample count for the physical sample that is identified as an absorbent gauze sponge.

20. The method of claim 2 wherein tagging the portion of the image of the sample with the blood volume indicator comprises tagging the portion of the image of the sample with an estimated hemoglobin mass.

21. The method of claim 20, wherein estimating the extracorporeal blood volume in at least the portion of the physical sample comprises estimating the extracorporeal blood volume in at least the portion of the physical sample according to the hemoglobin mass and an estimated hematocrit of the blood in the physical sample.

22. The method of claim 2, wherein estimating the extracorporeal blood volume in at least the portion of the sample comprises estimating the total extracorporeal blood volume in the physical sample based upon aggregated blood volume indicator tags of the portion of the image of the sample and substantially all other portions of the image.

23. The method of claim 22, further comprising estimating patient blood loss by aggregating the estimated total extracorporeal blood volume in the physical sample and estimated total extracorporeal blood volumes in additional physical samples in additional images.

24. The method of claim 22, further comprising estimating a volume of non-blood fluid in the physical sample by subtracting the weight of the estimated total extracorporeal blood volume in the physical sample from an entered weight of the physical sample.

25. The method of claim 4, wherein extracting the feature from the portion of the image of the sample comprises extracting the feature that comprises a color intensity value in a component space.

26. The method of claim 4, further comprising identifying the physical sample in the image as a type of absorbent gauze sponge.

27. The method of claim 26, further comprising indexing a sample count for the physical sample that is identified as an absorbent gauze sponge.

28. The method of claim 4 wherein tagging the portion of the image of the sample with the blood volume indicator comprises tagging the portion of the image of the sample with an estimated hemoglobin mass.

29. The method of claim 28, wherein estimating the extracorporeal blood volume in at least the portion of the physical sample comprises estimating the extracorporeal blood volume in at least the portion of the physical sample according to the hemoglobin mass and an estimated hematocrit of the blood in the physical sample.

30. The method of claim 4, wherein estimating the extracorporeal blood volume in at least the portion of the sample comprises estimating the total extracorporeal blood volume in the physical sample based upon aggregated blood volume indicator tags of the portion of the image of the sample and substantially all other portions of the image.

31. The method of claim 30, further comprising estimating patient blood loss by aggregating the estimated total extracorporeal blood volume in the physical sample and estimated total extracorporeal blood volumes in additional physical samples in additional images.

32. The method of claim 30, further comprising estimating a volume of non-blood fluid in the physical sample by subtracting the weight of the estimated total extracorporeal blood volume in the physical sample from an entered weight of the physical sample.

33. The method of claim 1, further comprising identifying the physical sample in the image as a type of absorbent gauze sponge.

34. The method of claim 33, further comprising indexing a sample count for the physical sample that is identified as an absorbent gauze sponge.

35. The method of claim 2, wherein tagging the portion of the image of the sample with the blood volume indicator comprises comparing the portion of the image of the sample with a template image of known extracorporeal blood volume indicator and associating the portion of the image of the sample with the blood volume indicator that is correlated with the known extracorporeal blood volume indicator of the template image.

36. The method of claim 35, wherein comparing the portion of the image of the sample with the template image comprises pairing the portion of the image of the sample and the template image via template matching.

37. The method of claim 36, wherein comparing the portion of the image of the sample with the template image comprises selecting the template image from a library of template images of known extracorporeal blood volume indicators.

38. The method of claim 36, wherein comparing the portion of the image of the sample with the template image comprises calculating the absolute difference in pixel intensity for a plurality of pixels in each of the portion of the image of the sample and the template image.

39. The method of claim 1, wherein tagging the portion of the image of the sample with the blood volume indicator comprises tagging the portion of the image of the sample with an estimated hemoglobin mass.

40. The method of claim 39, wherein estimating the extracorporeal blood volume in at least the portion of the physical sample comprises estimating the extracorporeal blood volume in at least the portion of the physical sample according to the hemoglobin mass and an estimated hematocrit of the blood in the physical sample.

41. The method of claim 2, wherein extracting the feature from the portion of the image of the sample comprises extracting the feature that comprises a color intensity value in a component space, and wherein tagging the portion of the image of the sample with the blood volume indicator comprises comparing the color intensity value of the portion of the image of the sample with intensity values of color models paired with known blood volume indicators.

42. The method of claim 41, wherein tagging the portion of the image of the sample with the blood volume indicator comprises generating the blood volume indicator tag that is a composite of known blood volume indicators of a plurality of color models.

* * * * *